United States Patent [19]
Ranscht

[11] Patent Number: 5,863,804
[45] Date of Patent: Jan. 26, 1999

[54] ANTIBODIES SPECIFICALLY REACTIVE WITH T-CADHERIN

[75] Inventor: Barbara Ranscht, Del Mar, Calif.

[73] Assignee: La Jolla Cancer Research Foundation, La Jolla, Calif.

[21] Appl. No.: 472,481

[22] Filed: Jun. 7, 1995

Related U.S. Application Data

[62] Division of Ser. No. 213,361, Mar. 14, 1994, Pat. No. 5,585,351, which is a continuation of Ser. No. 607,293, Oct. 30, 1990, abandoned.

[51] Int. Cl.$^6$ ............................ G01N 33/53; C07K 16/00
[52] U.S. Cl. .............................. 436/547; 436/548; 514/2; 514/8; 530/387.9; 530/388.1; 530/389.1
[58] Field of Search .............................. 530/387.1, 387.9, 530/388.1, 388.2, 389.1, 391.1, 391.3; 435/7.1, 7.2, 7.21, 7.92, 7.95, 70.1; 436/547, 548; 514/2, 8

[56] References Cited

PUBLICATIONS

Harlow et al "Antibodies: A Laboratory Manual", 1988 Cold Spring Harbor Press pp. 92–120 and 139–242.
Laemmti, Cleavage of structural proteins during the assembly of the head of bacteriophage T4. Nature 227:680–685 (1970).
Ranscht et al., A neuronal surface glycoprotein associated with the cytoskeleton, J. Cell. Biol. 99:1803–1813 (1984).
Edelman et al., Cellular expression of liver and neural cell adhesion molecules after transfection with their cDNAs results in specific cell–cell binding. Proc. Natl. Acad. Sci. USA 84:8502–8506 (1987).
Gallin et al., Sequence analysis of a cDNA clone encoding the liver cell adhesion molecule, L–CAM. Proc. Natl. Acad. Sci. USA 84:2808–2812 (1987).
Hatta et al., Spatial and Temporal Expression Pattern of N–cadherin cell adhesion molecules correlated with morphogenetic processes of chicken embryos. Dev. Biol. 120:215–217 (1987).
Nagafuchi et al., Transformation of cell adhesion properties by exogenously introduced E–cadherin cDNA. Nature 329:341–343 (1987).
Nose et al., Isolation of placental cadherin cDNA: identification of a novel gene family of cell–cell adhesion molecules. EMBO J. 6(12):3655–3661 (1987).
Ringwald et al., The structure of cell adhesion molecule uvomorulin. Insights into the molecular mechanism of $Ca^{3+}$– dependent cell adhesion. EMBO J. 6(12):3647 (1987).
Hatta et al., Cloning and expression of cDNA encoding a neural calcium–dependent cell adhesion molecule: its Identity in the cadherin gene family. J. Cell Biol. 106:873–881 (1988).
Mege et al., Construction of epithelioid sheets by transfection of mouse sarcoma cells with cDNAs for chicken cell adhesion molecules. Proc. Natl. Acad. Sci. USA 85:7274–7278 (1988).

Nagafuchi and Takeichi, Cell binding function of E–cadherin is regulated by the cytoplasmic domain. EMBO J. 7(12):3679–3684 (1988).
Neugebauer et al., N–cadherin, NCAM, and integrins promote retinal neurite outgrowth on astrocytes in vitro. Chem. Abstract 109:487, abstract No. 109:167903c (1988).
Takeichi, The cacherins: cell–cell adhesion molecules controlling animal morphogenesis. Development 102:639–655 (1988).
Kemler and Ozawa, Uvomorulin–catenin complex: cytoplasmic anchorage of a $Ca^{2+}$–dependent cell adhesion molecule. BioEssays 11(4):88–91 (1989).
Moss and White, A $Ca^{3+}$–sensitive glycoprotein, GP90, associated with the cytoskeleton from brain and gizzard. J. Cell Sci. 93:85–94 (1989).
Nagafuchi and Takeichi, Transmembrane control of cadherin–mediated cell adhesion: a 94 kDa protein functionally associated with a specific region of the cytoplasmic domain of E–cadherin. Cell Regulation 1:37–44 (1989).
Ozawa et al., The cytoplasmic domain of the cell adhesion molecule uvomorulin associates with three independent proteins structurally related in different species. EMBO J. 8(6):1711–1717 (1989).
Ranscht and Dours, Selective Expression of a novel cadherin in the pathways of developing motor and commissural axons. Society for Neuroscience Abstracts 15(part 1), abstract No. 382.6 (1989).
Bixby and Zhang, Purified N–cadherin is a potent substrate for the rapid induction of neurite outgrowth. J. Cell Biol. 110:1253–1260 (1990).
Matsuzaki et al., DNAs of cell adhesion molecules of different specificity induce changes in cell shape and border formation in cultured S180 cells. J. Cell Biol. 110:1239–1252 (1990).
McNeill et al., Novel function of the cell adhesion molecule uvomorulin as an inducer of cell surface polarity. Cell 62:309–316 (1990).
Nose et al., Localization of specificity determining sites in cadherin cell adhesion molecules. Cell 61:147–155 (1990).
Ozawa et al., Uvomorulin–catenin complex formation is regulated by a specific domain in the cytoplasmic region of the cell adhesion molecule. Proc. Natl. Acad. Sci. USA 87:4246–4250 (1990).
Ozawa and Kemler, Correct proteolytic cleavage is required for the cell adhesive function of uvomorulin. J. Cell Biol. 111:1645–1650 (1990).

(List continued on next page.)

Primary Examiner—Paula K. Hutzell
Assistant Examiner—Patricia A. Duffy
Attorney, Agent, or Firm—Campbell & Flores LLP

[57] ABSTRACT

The present invention provides antibodies specifically reactive with T-cadherin, but not with N-, E- or P-cadherin. The present invention also provides methods of obtaining such antibodies by administering to an animal a synthetic peptide or a recombinant protein fragment having a partial sequence of T-cadherin. The present invention further provides antibodies obtained by such methods.

9 Claims, 18 Drawing Sheets

OTHER PUBLICATIONS

Ozawa et al., Single amino acid substitutions in one $Ca^{2+}$ binding site of uvomorulin abolish the adhesive function. Cell 63:1033–1038 (1990).

Takeichi, Cadherins: a molecular family important in selective cell–cell adhesion. Annu. Rev. Biochem. 59:237–252 (1990).

Ranscht, Cadherin cell adhesion molecules in vertebrate neural development. Seminars in The Neurosciences 3:285–296 (1991).

Ranscht and Dours–Zimmermann, T–cadherin, a novel cadherin cell adhesion molecule in the nervous system lacks the conserved cytoplasmic region. Neuron 7:391–402 (1991).

```
  1      GAATTCCGAATGAAAAGCCCTCTGGTACGTTCCTAGTCTGGCAAAATGCAGCACAAAACTCAACTTACTCTGTCCTTTCTGCTGTCCCAG
-22                                              M  Q  H  K  T  Q  L  T  L  S  F  L  L  S  Q

90      GTTCTGTTGCTTGCCGTGTGCAGAAGATTAGAATGCACCCCCTGATTCCAGCAAAAGTTTTTATATTGAACAGCCATTTGAATTCACA
 -7      V  L  L  A  C  A  E  D  L  E  C  T  P  G  F  Q  Q  K  V  F  Y  I  E  Q  P  F  E  F  T

180      GAGGACCAGCCAATTCTGAACCTGGTGTTTGATGACTGCAAGGGGAATAACAAATTGAACTTCGAAGTTTCTAACCCAGACTTTAAGGTG
 24      E  D  Q  P  I  L  N  L  V  F  D  D  C  K  G  N  N  K  L  N  F  E  V  S  N  P  D  F  K  V

270      GAACACGATGGATCTTTAGTTGCACTGAAGAATGTATCAGAAGCTGGCAGAGCTTTGTTTGTCCATGCACGGTCTGAGCATGCTGAGGAT
 54      E  H  D  G  S  L  V  A  L  K  N  V  S  E  A  G  R  A  L  F  V  H  A  R  S  E  H  A  E  D

360      ATGGCAGAAATTTTGATTGTTGGAGCTGATGAGAAGCACGATGCATTAAAGGAAATCTTTAAGATAGAAGGCAACCTTGGAATTCCAAGA
 84      M  A  E  I  L  I  V  G  A  D  E  K  H  D  A  L  K  E  I  F  K  I  E  G  N  L  G  I  P  R

450      CAAAAAAGGGCTATTCTGGCGACTCCAATATTAATTCCAGAAAATCAAAGACCACCATTTCCAGGAGTTGGCAAGGTCATCAGGAGT
114      Q  K  R  A  I  L  A  T  P  I  L  I  P  E  N  Q  R  P  P  F  P  P  R  S  V  G  K  V  I  R  S

540      GAAGGGACAGAGGGAGCAAAGTTCCGACTCTCTGGTAAGGGAGTAGATCAAGACCCGAAAGGAATTTTAGAATCAATGAGATCAGTGGG
144      E  G  T  E  G  A  K  F  R  L  S  G  K  G  V  D  Q  D  P  K  G  I  F  R  I  N  E  I  S  G

630      GATGTCTCTGTGACCCGACCCTGGATAGAGAAGCAATAGCAAATTATGAGCTGGAAGTTGAAGTAACGGATTTAAGTGGGAAAATCATT
174      D  V  S  V  T  R  P  L  D  R  E  A  I  A  N  Y  E  L  E  V  T  D  L  S  G  K  I  I

720      GATGCCCAGTCCGCTTAGATATTTCTGTTATTGATCAAAATGATAACAGGCCGATGTTCAAAGAAGGACCCTATGTTGGTCACGTCATG
204      D  A  Q  S  R  L  D  I  S  V  I  D  Q  N  D  N  R  P  M  F  K  E  G  P  Y  V  G  H  V  M

810      GAAGGATCCCCTACAGGAACACTTGTCATGAGGATGACAGCATTTGATGCTGATGATCCTAGCACAGACAACGCTCTCTTGCGGTATAAC
234      E  G  S  P  T  G  T  T  V  M  R  M  T  A  F  D  A  D  D  P  S  T  D  N  A  L  L  R  Y  N

900      ATCCTCAAGCAGACCCCTACCAAAACCTTCCCCAAATATGTTCTACATTGACCCAGAAAAGGGAGATATTGTCACAGTGGTGTCACCTGTA
264      I  L  K  Q  T  P  T  K  P  S  P  N  M  F  Y  I  D  P  E  K  G  D  I  V  T  V  V  S  P  V

990      CTGCTGGATCGTGAGACAATGGAAACGCCAAGTACGAAGCCAAGGATATGGGCGGCCATGATGTGGGACTTACTGGA
294      L  L  D  R  E  T  M  E  T  P  K  Y  E  L  V  I  E  A  K  D  M  G  G  H  D  V  G  L  T  G
```

```
  1        GAATTCCAAAAGCCCTCTGGTACGTTCTAGTCTGGCAAAATGCAGCACAAACTCAACTTACTCTGTCTTCTTCTGTCTGTCCAGTTCTG
-22                                        M  Q  H  K  T  Q  L  T  L  S  F  L  L  S  Q  V  L

91        TTGCTTGCGTGTGCAGAAGATTTAGAATGCACCCCTGGATTCCAGCAAAAGTTTTTTATATTGAACAGCCATTTGAATTCACAGAGAC
 -5        L  L  A  C  A  E  D  L  E  C  T  P  G  F  Q  Q  K  V  F  Y  I  E  Q  P  F  E  F  T  E  D

181        CAGCCAATTCTGAACCTGGTGTTTGATGATTGTAAGGGGAATAACAAATTGAACTTCGAAGTTTCTAACCCAGACTTTAAGGTGGAACAC
 26        Q  P  I  L  N  L  V  F  D  D  C  K  G  N  N  K  L  N  F  E  V  S  N  P  D  F  K  V  E  H

271        GATGGATCTTTAGTGGCACTGAAGAATGTATCAGAAGCTGGCAGAGCTTTGTTTGTCCATGCACGGTCTGAGCATGCTGAGGATATGGCA
 56        D  G  S  L  V  A  L  K  N  V  S  E  A  G  R  A  L  F  V  H  A  R  S  E  H  A  E  D  M  A

361        GAAATTTGATTGTTGGAGCTGATGAGAAGCACGATGCATTAAAGGAAATCTTTAAGATAGAAGGCAACTTGGAATTCCAAGACAAAAA
 86        E  I  L  I  V  G  A  D  E  K  H  D  A  L  K  E  I  F  K  I  E  G  N  L  G  I  P  R  Q  K

451        AGGGCTATTCTGGCGACTCCAATATTAATTCCAGAAATCAAAGACCCATTCCCAGATCAGTTGGCAAGGTCAGTCATCAGGAGTGAAGG
116        R  A  I  L  A  T  P  I  L  I  P  E  N  Q  R  P  P  F  P  R  S  V  G  K  V  I  R  S  E  G

541        ACAGAGGAGCAAAGTTCCGACTCTCTGTAAGGAGTAGATCAAGAGGAATTTTAGAATCAATGAGATCAGTGGGATGTC
146        T  E  G  A  K  F  R  L  S  G  K  G  V  D  Q  D  P  K  G  I  F  R  I  N  E  I  S  G  D  V

631        TCTGTGACCCGACCCCTAGATAGAGAAGCAATAGCAAATTATGAGTTAGAAGTAACGGATTTAAGTGGAAAAATCATTGATGGC
176        S  V  T  R  P  L  D  R  E  A  I  A  N  Y  E  L  E  V  T  D  L  S  G  K  I  I  D  G

721        CCAGTCCGCTAGATATTTCTGTTATTGATCAAAATGATAACAGGCCGATGTTCAAAGAAGGACCCTATGTTGGTCACGTCATGGAAGGA
206        P  V  R  L  D  I  S  V  I  D  Q  N  D  N  R  P  M  F  K  E  G  P  Y  V  G  H  V  M  E  G

811        TCCCCTACAGGAACAACTGTGATGCGGATGACAGCATTTGATGCTGATGATCCTAGCACAGACAACGCTCTTCGCGTATAACATCTC
236        S  P  T  G  T  T  V  M  R  M  T  A  F  D  A  D  D  P  S  T  D  N  A  L  L  R  Y  N  I  L

901        AAGCAGACACCTACCAACCTTCCCAAATGTTCTACATTGACCCAGAAAAGGGAGATATTGTCACAGTGGTGTCGCCTGTACTGCTG
266        K  Q  T  P  T  K  P  S  P  N  M  F  Y  I  D  P  E  K  G  D  I  V  T  V  V  S  P  V  L  L

991        GATCGTGAGACAATGGAAACGCCGAAGTACGAGCTGGTTATTGAAGCCAAGGATATGGGCGGCCATGATGTGGGACTTACTGAACTGCA
296        D  R  E  T  M  E  T  P  K  Y  E  L  V  I  E  A  K  D  M  G  G  H  D  V  G  L  T  G  T  A
```

```
1081  ACTGCCACTATTCTTATTGATGACAAAAACGACCACCCAGATTACCAAGAGGAGTTTCAGGCCACAGTAAGGAAGGAGTCACA
 326   T  A  T  I  L  I  D  D  K  N  D  H  P  P  E  F  T  K  K  E  F  Q  A  T  V  K  E  G  V  T

1171  GGAGTAATAGTAAACTTAACTGTTGGTGACCGAGATGACCCAGCTACCGGAGCATGGAGAGCTGTCTACACTATTATTAACGGAAATCCA
 356   G  V  I  V  N  L  T  V  G  D  R  D  D  P  A  T  G  A  W  R  A  V  Y  T  I  I  N  G  N  P

1261  GGGCAGAGTTTGAAATCATACCAATCCCCAGACTAATGAGGAATGCTCTCTGTTGTCAAACCTTTAGACTATGAGATTTCAGCATTT
 386   G  Q  S  F  E  I  H  T  N  P  Q  T  N  E  G  M  L  S  V  V  K  P  L  D  Y  E  I  S  A  F

1351  CACACATTGCTGATAAAGTAGAAAATGAAGACCCGTTGATTCCAGACATAGCCTACGGTCCCAGTTCCACAGCAACAGTTCAGATCACC
 416   H  T  L  L  I  K  V  E  N  E  D  P  L  I  P  D  I  A  Y  G  P  S  S  T  A  T  V  Q  I  T

1441  GTTGAGGATGTGAATGAAGGCCCCGTGTTTCCACCCAAACCAATGACAGTGACAAAACAAGAGAACATCCCTATTGGCAGCATTGTGTTA
 446   V  E  D  V  N  E  G  P  V  F  H  P  N  P  M  T  V  T  K  Q  E  N  I  P  I  G  S  I  V  L

1531  ACAGTAAATGCCACTGATCCAGATACTTTGCAACATCAGTTACAAGGATCTATTCAGTTCAGTATACAGATCTGGCTAGAGATTAAT
 476   T  V  N  A  T  D  P  D  T  L  Q  H  Q  T  I  R  Y  S  V  Y  K  D  P  A  S  W  L  E  I  N

1621  CCCACCAATGGTACCGTTGCCACCACTGCTGTCCTGGATCGGGAATCCCATGTTCAGGATAACAAATACTGCTCTCTCCTGGCA
 506   P  T  N  G  T  V  A  T  T  A  V  L  D  R  E  S  P  H  V  Q  D  N  K  Y  T  A  L  F  L  A

1711  ATAGACAGTGGTAACCCTCCTGCTACAGGTACAGGAACTTTACACATCACCTTGGAGGACGTCAATGACAATGTCCCCTTTACCCA
 536   I  D  S  G  N  P  P  A  T  G  T  G  T  L  H  I  T  L  E  D  V  N  D  N  V  P  S  L  Y  P

1801  ACACTGGCAAAAGTCTGTGATGATGCTAAAGATCTTAGAGTAGTGTTCTAGGAGCATCAGACACAAAGACCTCCATCCAACACAGATCCA
 566   T  L  A  K  V  C  D  D  A  K  D  L  R  V  V  L  G  A  S  D  K  D  L  H  P  N  T  D  P
```

```
SIG  T  MQHKTQLTLSFLLSQVL.LLACA.....
     N  MCRIAGTPPRILPPLALMLLAALQQAPI
     L  ...........................
     E  MGARCRSFSALLLLLLQVSSWLCQELEP.
     P  MELLSGPHAFLLLLLQVCWLRSVVSEP.

PRE  T  ....EDLECTPGFQQKV.FYIEQPFEFTE.DQPILNLVFDDQKGNNKLNFEVSNP.DFKVEHDCSLVA.L
     N  KATCEDMLCKMGFPEDV.HSAVVSRSVHG.GQPLLNVRFQSCDENRKIYFGSSEPEDFKVGEDCVVYAER
     L  ......................DSVAA.GRELGRVSFAACS.GRPWAVYVPTDTRFKVNGDCVVSTKR
     E  ......ESCSPGFSSEV.YTFPVPERHLERGHVLGRVRFEGCT.GRPRTAFFSEDSRFKVATDGTITVKR
     P  ........YRAGFIGEAGVTLEVEGTDLEPSQVLGKVALAGQG............................

EC1  T  AILATPILIPENQR.PPFPRSVGKVIRSEGTEGA.....KFRLS..GKCVDQDPKGIFRINEIS.....G
     N  DWVIPPINLPENSR.GPFPQELVR.IRSDRDKSL.....SLRYSVTGPGADQPPTGIFIINPIS.....G
     L  DWVIPPISCLENHR.GPYPMRLVQ.IKSNKDKES.....KVYYSITGQGADSPFVGIFIIERET.....G
     E  DWVIPPISCPENEK.GEFPKNLVQ.IKSNRDKET.....KVFYSITGQGADKPPVGVFIIERET.....G
     P  EWVMPPIFVPENGK.GPFPQRLNQ.LKSNKDRGT.....KIFYSITGPGADSPPEGVFTIEKES.....G
        **  **      *        *            *  * *  * *   *               *

EC2  T  KEGPYVGHVMECSPTGTTVM...RMTAFDADD.PSTDNALLRYNILKQTPTKPSPNMFYIDPEK.....G
     N  LHQVWNGTVPEGSKPGTYVM...TVTAIDADD.PNAQNGMLRYRILSQAPSSPSPNMFTINNET.....G
     L  IKEVFVGYIEENAKPGTSVM...TVNATDADDAVNTDNGIVSYSIVSQQPPRPHPQMFTIDPAK.....G
     E  TQEVFEGSVAEGAVPGTSVM...KVSATDADDDVNTYNAAIAYTIVSQDPELPHKNMFTVNRDT.....G
     P  TQDTFRGSVIEGVMPGTSVM...QVTATDEDDAVNTYNGVVAYSTHSQEPKEPHDLMFTIHKST.....G
        *   *   ** **         *    **    *   * *   *   *    *     **         *

EC3  T  TKKEFQATVKEG.VTGVIV.NL.TVG..DRDD.PATGAWRAVYTIINGN...P.GQSFEIHTNPQTNE.G
     N  TAMTFYGEVPEN.RVDVIVANL.TVT..DKDQ.PHTPAWNARYQMTGGD...PTGQ.FTILTDPNSND.G
     L  NPTMYEGVVEEN.KPGTEVARL.TVT..DQDA.PGSPAWQAVYHIKSGN...LDGA.FSIITDPSTNN.G
     E  NPSTYQGQVPEN.EVNARIATL.KVT..DDDA.PNTPAWKVVYTVV.ND...PDQQ.FVVVTDPTTND.G
     P  EPQKYEAWVPEN.EVGHEVQRL.TVT..DLDV.PNWPAWRATYHIVGGD...DGDH.FTITTHPETNQ.G
        *  *         *  *   * *    *    *  * *  *                 *  * *   *

EC4  T  HPNPMTVTKQENIPIGSIVL...TVNATDPDTLQHQT...IRYSVYKD....PASWLEI...NPTN...G
     N  VPNPKLVRQEEGLLAGSMLT...TFTARDPDRYMQQT..SLRYSKLSD....PANWLKI...DPVN...G
     L  VPPIKRVGVPEDLPVGQQVT...SYTAEDPDRDMRQ...KITYRMGSD....PAGWLYI...HPEN...G
     E  MPAERRVEVPEDFGVGQEIT...SYTAREPDTFMDQ...KLTYRIWRD....TANWLEI...NPET...G
     P  VPPSKVIEAQEGISIGELVC...IYTAQDPDKE.DQ...KISYTISRD....PANWLAV...DPDS...G
           *        *        * *    *        * *  *         *  *

EC5  T  SLYPTLAKVCDDAKDLRVV....VLGASDKDLHPNTDPFKFELSKQSGPE..KL.W..RINKLN..NTHA
     N  QVNPKEATTCETLQPNAIN.....ITAVDPDIDPNAGPFAFELPD.SPPSI.KRNW..TIVRIS..GDHA
     L  TPEPRSFEICSR.QPEKQI.....LSIVDKDLPPHTYPFKAALEH.GSS....NNW..TVEIRG..QDEL
     E  IPEPRNMQFCQR.NPQPHI.....ITILDFDLPPNTSPFTAELTH.GAS....VNW..TIEYNDAAQESL
     P  IPEPRQIIICNQ.SPVPQV.....LNITDKDLSPNSSPFQAQLTH.DS.DI...YW..MAEVSE.KGDTV
        *  *                  *   *    *  *   *    *              *

TM   T  .......ALHISMTLILLSLFSLFCL*
     N  ..IVGAGLGTGAIIAILLCIIILLILVLMFVVWM
     L  ..IVG.GLGVPAILGILGGILALLILLLLLLFA
     E  AGIVAAGLQVPAILGILGGILALLILILLLLLFL
     P  ....G.GFILP.ILGAV...LALLTLLLALLLLV
                           *  *

CP   T
     N  KRRDKERQAKQLLIDPEDDVRDNILKYDEEGGGEEDQDYDLSQLQ.QPDTVEPDAIKPVGIRRLDERP.IHAEPQYPVRSAAP
     L  RRRKVEKEP..LLP.PEDDMRDNVYNYDEEGGGEEDQDYDLSQLHRGLDAR.PEVI......RNDVAPPLMAAPQYRPRPA..
     E  RRRTVVKEP..LLP.PDDDTRDNVYYYDEEGGGEEDQDFDLSQLHRGLDAR.PEVT......RNDVAPTLMSVPQYRPRPA..
     P  RKKRKVKEP..LLL.PEDDTRDNVFYYGEEGGGEEDQDYDITQLHRGLEAR.PEVVL.....RNDVVPTFIPTPMYRPRPA..

T
     N  HPGDIGDFINEGLKAADNDPTAPPYDSLLVFDYEGSGSTAGSLSSLNSSSSGGEQDYDYLNDWGPRFKKLADMYGGG.DD*
     L  NPDEIGNFIDENLKAADTDPTAPPYDSLLVFDYEGGGSEATSLSSLNSSASDQDQDYDYLNEWGNRFKKLAELYGGGEDDE*
     E  NPDEIGNFIDENLKAADSDPTAPPYDSLLVFDYEGSGSEAASLSSLNSSESDQDQDYDYLNEWGNRFKKLADMYGGGEDD*
     P  NPDEIGNFIIENLKAANTDPTAPPYDSLMVFDYEGSGSDAASLSSLTTSASDQDQDYNYLNEWGSRFKKLADMYGGGEDD*
```

FIG.3A

```
KNVSEAGRALF..VHAR..SEHAE...DMAEILI.VGADEKHDALKEIFKIEGNLGIP..........RQKR
SFQLSAEPTEFVVSARDKETQEEWQMKVKLT.PEPAFTGASEKDQKKIEDIIFPWQQYKDSSHLKRQKR
PLTLYGRKISFTIYAQDAMGKR.HSARVTV..GRHRHRRHHHNHHLQDTTPAVLTFPKHDPGFLRRQKR
HLKLHKLETSFLVRARDSSHRE.LSTKVTLKSMGHHHHRHHHRDPASESNPELLMFPSVYPG.LRRQKR
...............................MHHADNGDIIMLTRGTVQGGKDAMHSPPTRILRRRKR
                                                                * **

DVSVTRP...LDRE.....AIANYELEVEVTDLSGKIIDG.........PVRLDISVIDQNDNRPMF
QLSVTKP...LDRE.....QIASFHLRAHAVDVNGNQVEN.........PIDIVINVIDMNDNRPEF
WLEVTEQ...LDRE.....KIDRYTLLSHAVSASGQPVED.........PMEIITTVMDQNDNKPVF
WLKVTQP...LDRE.....AIAKYILYSHAVSSNGEAVED.........PMEIVITVTDQNDNRPEF
WLLLHMP...LDRE.....KIVKYELYGHAVSENGASVEE.........PMNISIIVTDQNDNKPKF
          ****      *    *      *                *   *  * ** *  *

DIVTVVSPVLLDRE...TMETPKYELVIEAKDMGGHDV..GLTG.....TATATILIDDKNDHPPEF
DIITVAAG..LDRE.....KVQQYTLIIQATDMEGNPTY.GLSN.....TATAVITVTDVNDNPPEF
IISVLGTG..LDRE.....TTPNYTLIVQATDQEGK....GLSN.....TATALIEVTDANDNIPIF
VISVLTSG..LDRE.....SYPTYTLVVQAADLQGE....GLST.....TAKAVITVKDINDNAPVF
TISVISSG..LDRE.....KVPEYRLTVQATDMDGE....GSTT.....TAEAVVQILDANDNAPEF
*         ****       *   * *   *         *      ** *    * **  * *

.MLSVVKP..LDYE.....ISAFHTLLI.KVE.NEDPLIPDIAYGPSS.TATVQITVEDVNE.GPVF
.LVTVVKP..IDFE.....TNRMFVLTV.AAE..NQVPLAKGIQHPPQS.TATVSITVIDVNE.SPYF
ILKTA.KG..LDYE.....TKSRYDLVV.TVE.NKVPLS.VPITLS...TASVLVTVLDVNE.PPVF
ILKTA.KG..LDFE.....AKQQYILHV.RVE.NEEPFE.GSLVPS...TATVTVDVVDVNE.APIF
VLTTK.KG..LDFE.....AQDQHTLYV.EVT.NEAPFA.VKLPTA...TATVVVHVKDVNE.APVF
       *  * *              *   *                 ** *  * **** * *

TVATTAV...LDRESP.HVQDNKYTALFLAID.SGNPPATG........TGTLHITLEDVNDNVP
QITTTAV...LDRESI.YVQNNMYNATFLASD.NGIPPMSG........TGTLQIYLLDINDNAP
.IVTATQP..LDRESV.HAINSTYKAIILAVD.NGIPDTTG........TGTLLLLLQDVNDNGP
AIFTRAE...MDREDAEHVKNSTYVALIIATD.DGSPIATG........TGTLLLVLLDVNDNAP
QI.TAAGI..LDREDEQFVKNNVYEVMVLATD.SGNPPTTG........TGTLLLTLTDINDHGP
           ***       *    * * *        *        ****  * **   *

QVVL..LQNLKKAN........YNIPISVTD.SGKPPLTNNTELKLQVCSCK.KSRMDCSASD.
QLSL..RIRFLEAGI.......YDVPIVITD.SGNPHASSTSVLKVKVCQCD.ING.DCTDVDR
AMGL...KKELEPGE.......YNIFVKLTD.SQGK.AQVTQV.KAQVCECEGTAKN.CERRSY
ILQP...RKDLEIGE.......YKIHLKLAD.NQNKD.QVT.TLDVHVCDCEGTVNN.CMK...
ALSL...KKFLKQDT.......YDLHLSLSD.HGNRE.QLT.MIRATVCDCHGQVFNDCPRPWK
          *            *   *  *                  ** *      *
```

FIG.3B

ANTIBODIES SPECIFICALLY REACTIVE WITH T-CADHERIN

This is a division of application Ser. No. 08/213,361, filed Mar. 14, 1994, now U.S. Pat. No. 5,585,351, which was a continuation of application Ser. No. 07/607,293, filed Oct. 30, 1990, now abandoned.

BACKGROUND OF THE INVENTION

This invention relates to cell surface molecules and more specifically to T-cadherin, a new cell adhesion molecule of the cadherin family.

Cadherins are a family of transmembrane glycoproteins that mediate adhesive interactions in the developing and adult organism through a Ca2+-dependent mechanism (Takeichi, 1988 and 1990, review). It has been suggested that the cadherins arose from a common ancestral gene. Duplication of the gene may have resulted in the formation of a structurally related family of molecules with heterogeneous sequences. Cadherins share their overall structure which, at the extracellular region, is subdivided into a signal peptide, a prepeptide and five related extracellular domains and is followed by a transmembrane domain and a highly conserved stretch of cytoplasmic amino acids, that is suggested to provide a linkage with the cell's cytoskeletal network. The signal peptide and the prepeptide are readily cleaved and are absent from the mature protein. Several members of the cadherin family have been characterized. N-cadherin is found in the nervous system during development and has been shown to be a strong mediator of nerve fiber growth in vitro. In addition to neural tissue, N-cadherin is also expressed in heart and skeletal muscle and in lens cells. E-cadherin (also known as uvomorulin in the mouse) is a component of epithelial cells and P-cadherin is found in placenta.

T-cadherin, which is subject of this application, is novel member to the cadherin family that shares the overall cadherin structure in the extracellular region, but lacks the conserved cytoplasmic sequences. Therefore a new mode of T-cadherin function is proposed, in which T-cadherin regulates the adhesive cell properties not through a direct linkage with the cytoskeleton, but through higher membrane mobility and ready access to its extracellular ligand. The pattern of T-cadherin expression suggests a key role in the establishment of the pattern of nerve fiber growth in developing embryos. Furthermore, T-cadherin is the first molecularly characterized polypeptide to be identified in a segmental pattern as epithelial somites undergo the transition to form the dermamyotome and sclerotome. The expression in only one half of the somitic sclerotome, that eventually will give rise to vertebrae, suggests that T-cadherin plays a key role in the segmentation of vertebrate embryos. Segmentation is a crucial property of the vertebral column that allows flexibility and provides an individual with the ability to bend the back. T-cadherin has also been identified in muscle cells and blood vessels. In muscle, T-cadherin may be involved in cell differentiation and function. Expression in blood vessels may suggest that T-cadherin may be associated with the vascularization of tumors. A tumor remains small unless provided with blood capillaries. The control of vascularization that may be possible with the reagents described in this invention, may therefore be useful in controlling tumor formation and metastasis.

The identification of molecules which regulate and direct nerve fiber growth is important to the study of nerve regeneration. After being severed, neurons either degenerate or remain in a state of severe atrophy. The prognosis for recovery of these damaged neurons is very poor. Therefore, the use of molecules such as the T-cadherin cell adhesion molecules may influence neurons to regrow their axons and guide the axons to reinnervate their corresponding target cells. Eventually, this may lead to relief from the disabling effects of stroke or trauma to the nervous system.

There thus exists a need for the identification and characterization of cell surface adhesion molecules which may be involved in regulation of development in the embryo or recovery of traumatized neurons including methods of detecting and utilizing these molecules. The present invention satisfies this need and provides related advantages as well.

SUMMARY OF THE INVENTION

The invention provides substantially purified T-cadherin polypeptides and isolated nucleic acids which encode the T-cadherin polypeptides. Antibodies reactive with various forms of T-cadherin, but not reactive with N-, E- or P-cadherin are also provided. The invention provides methods for detecting the various forms of T-cadherin in a subject as well as a method of detecting tumor growth which consists of inhibiting the activity of T-cadherin in a tumor. A method of effecting traumatized neurons is provided. The method entails treating traumatized neurons with a therapeutically effective dose of T-cadherin.

BRIEF DESCRIPTION OF THE DRAWINGS

FIGS. 2a to 2f show the nucleotide and predicted amino acid sequence of the T-cadherins. FIGS. 2a, 2b and 2c are the sequences of T-cadherin 1 (SEQ ID NO 1 and 2). FIGS. 2d, 2e and 2f show the sequences for T-cadherin 2 (SEQ ID NO 3 and 4).

FIGS. 3a and 3b show the amino acid alignment of T-cadherin 1 (SEQ ID NO 2) (266 cDNA) with the related proteins N-cadherin (SEQ ID NO 5), L-CAM (SEQ ID NO 6), E-cadherin (SEQ ID NO 7) and P-cadherin (SEQ ID NO 8).

DETAILED DESCRIPTION OF THE INVENTION

Figure 1:
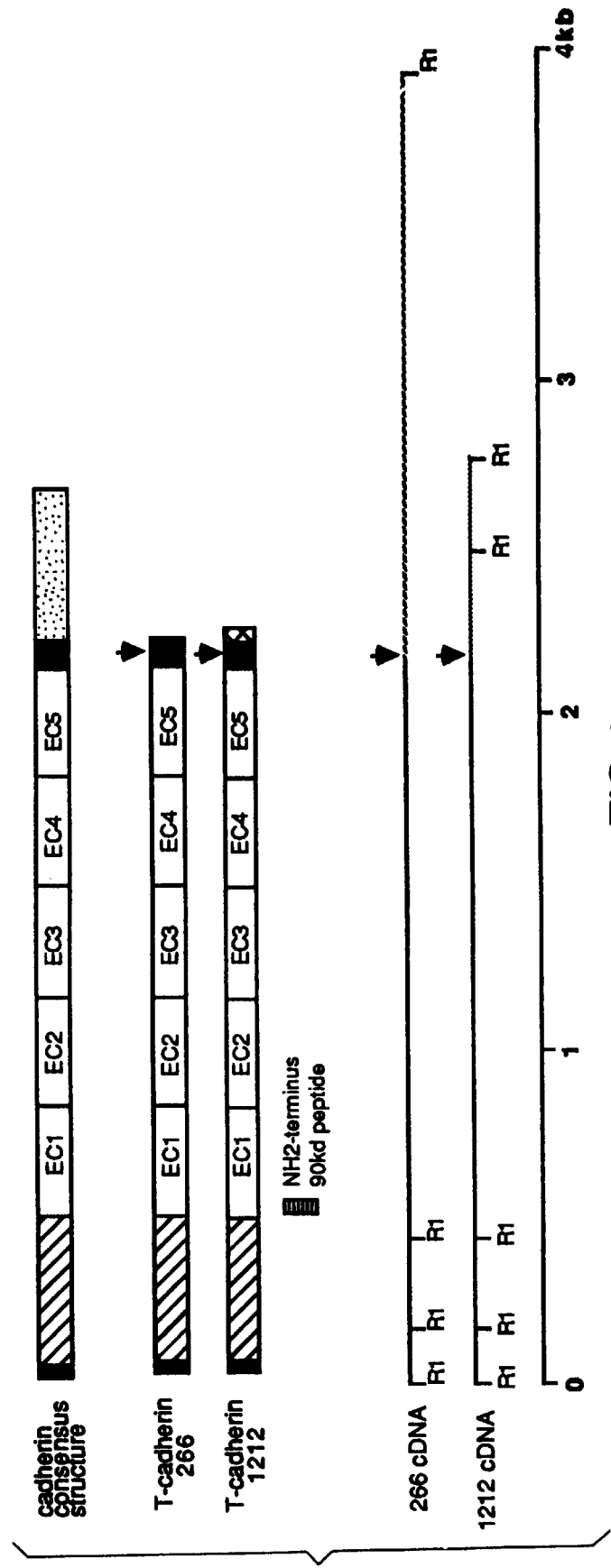
FIG. 1 shows the STRUCTURAL alignment of T-cadherin 1 (266 CDNA) and T-cadherin 2 (1212 CDNA) with the cadherin consensus structure.

T-cadherin ("T-cad;" T=truncated) is a member of the cadherin family of cell adhesion molecules. T-cadherin may be involved in the development of the embryo or recovery of traumatized neurons and therefore may be useful in nerve regeneration. T-cadherin is expressed in the nervous system, as well as the heart, skeletal muscle, blood vessels and the muscle lining the gut and skin. The high expression of T-cadherin in blood vessels may be important in the development of highly vascularized tumors.

T-cadherin shares some but not all structural features of other cadherins. The structural similarity extends to the amino acid level in that the extracellular portion of T-cadherin shows 35–47% identity with the extracellular domains of N-cadherin, E-cadherin, P-cadherin and L-CAM; N-cadherin with 47% amino acid identity being most closely related. Two forms of T-cadherin identified in the present invention lack the cytoplasmic portion found in all other members of the cadherin family. One form of T-cadherin, herein referred to as T-cad 1, appears to be anchored to the membrane through a glycosyl phosphatidylinositol (GPI) linkage. Biochemical evidence for such a linkage has been obtained by showing that T-cadherin can be released from the cellular plasma membrane by phosphatidylinositol specific phospholipase C and can incorporate radiolabeled ethanolamine into the GPI linkage. The other form of T-cadherin, T-cad 2, is predicted by the CDNA to contain sequences for a hydrophobic domain followed by 5 cytoplasmic amino acids. From preliminary transfection of this CDNA into COS-cells, it is likely that this form is also GPI-linked. These data provide evidence for a membrane linkage of T-cadherins that differs from known cadherins, in particular, in their proposed association with the cytoskeleton. In summary, T-cadherin is a member of the cadherin family of cell adhesion molecules that differs in its anchorage to the plasma membrane from known cadherins.

cDNAs have been isolated that encode T-cad (SEQ ID NO 1) 1 and T-cad 2 (SEQ ID NO 3), two closely related, but distinct forms of T-cadherin (FIGS. 2a to 2c and FIGS. 2d to 2f, respectively). The extracellular portion of both forms are identical and contain structural features characteristic of the cadherin family. The two forms differ in their COOH-terminal region in that T-cad 2 cDNA encodes five additional amino acids (FIGS. 3a and 3b). The absence of a cytoplasmic domain can allow for greater mobility of these molecules within the cell membrane and therefore modulate adhesive cell properties.

RNA transcripts encoding both forms of T-cadherin have been detected using RNAse protection probes specific for each form. There is evidence that the different forms of T-cadherin may be developmentally regulated both temporally and in a tissue specific fashion.

As used herein, "T-cadherin" or "T-cad" refers to polypeptides having substantially the amino acid sequence in FIGS. 2a to 2c and FIGS. 2d to 2f and which are cross-reactive with antibodies reactive with T-cad, but not with N-cadherin, E-cadherin, P-cadherin and L-CAM. Polypeptides comprising the extracellular, transmembrane and truncated cytoplasmic domain of T-cad 1 and T-cad 2 are provided. Minor modifications of the sequence which do not destroy its immunoreactivity also fall within the definition of the protein claimed.

The suggested open reading frame of T-cadherin cDNAs, T-cad 1 and T-cad 2, encode 690 and 695 amino acid proteins, respectively, of predicted molecular mass 76,018 and 76,627 daltons.

It is understood that limited modifications may be made without destroying the biological function of T-cadherin, and that only a portion of the entire primary structure may be required to effect activity. Minor modifications of the primary amino acid sequence may result in proteins which have substantially equivalent or enhanced function.

As used herein, "T-cadherin" refers to a cell adhesion polypeptide having an amino acid sequence substantially equivalent to that shown in FIGS. 2a (SEQ ID NO 2), and 2b (SEQ ID NO 4) and may be involved in the development of the embryonal nervous system and in recovery of traumitized neurons.

"Substantially purified," when used to describe the state of T-cadherin, denotes the protein substantially free of the other proteins and molecules normally associated with or occurring with T-cadherin in its native environment.

"Nucleic acid encoding" as used herein, refers to the primary nucleotide sequence of a gene which provides the order of corresponding amino acids in the protein that they specify. Examples of the cadherin nucleic acid sequence are presented in FIGS. 2a to 2c (SEQ ID NO 1) and, FIGS 2d to 2f (SEQ ID NO 3).

The invention provides nucleic acids (DNA, RNA, or cDNA) encoding the polypeptides of the invention. The nucleic acid may or may not be expressed in the native host. Vectors comprising these nucleic acids are also provided. Numerous cloning vectors are known to those of skill in the art, and the selection of an appropriate cloning vector is a matter of choice. "Transformed host cells" refers to cells which have had vectors, constructed using recombinant DNA techniques, introduced to them. Host cells can be transformed with such a vector and used to express recombinant polypeptides. Host cells can be mammalian, yeast, insect, or bacterial as long as the appropriate vector is used. Methods of recombinant expression are well known in the art, see Maniatis et al., MOLECULAR CLONING: A LABORATORY MANUAL (1982), which is incorporated herein by reference. Thus, recombinant polypeptides and the method of their production are also provided.

The vectors and methods disclosed herein are suitable for use in host cells including a wide range of prokaryotic and eukaryotic organisms. It is understood that "cells" or "host cells" refers not only to the particular subject cell, but also to the progeny of such a cell. The invention provides vectors which are capable of expressing DNA sequences contained therein, where such sequences are operably linked to other sequences capable of effecting their expression. It is implied that these expression vectors must be replicable in the host organism either as episomes or as an integral part of the chromosomal DNA.

Additionally, recombinant DNA methods currently used by those skilled in the art include the polymerase chain reaction (PCR), which, combined with the synthesis of oligonucleotides, allows easy reproduction of DNA sequences. A DNA segment can be amplified exponentially starting from as little as a single gene copy by means of PCR. In this procedure, a denatured DNA sample is incubated with two oligonucleotide primers that direct the DNA polymerase-dependent synthesis of new complementary strands. Multiple cycles of synthesis each results in an approximate doubling of the amount of target sequence. After twenty-five amplification cycles, the amount of target sequence increases by approximately $10^6$-fold. Amplification of first strand cDNAs using the polymerase chain reaction has been used to detect both forms of T-cadherin. The PCR technology is the subject matter of U.S. Pat. Nos. 4,683,195; 4,800,159; 4,754,065 and 4,683,202, all of which are incorporated by reference herein. The cDNAs shown in FIGS. 2a to 2c and 2d to 2f, or any portion of the sequence can be reproduced for cloning and expression purposes by amplifying the desired sequence with PCR and cloning it into a suitable vector, as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art.

Polyclonal antibodies against T-cadherin were prepared according to procedures well known in the art. The specificity of the antibodies was examined by carrying out immunohistochemistry and immunoblotting of various tissues including neuronal cells and somites.

Figure 2B:
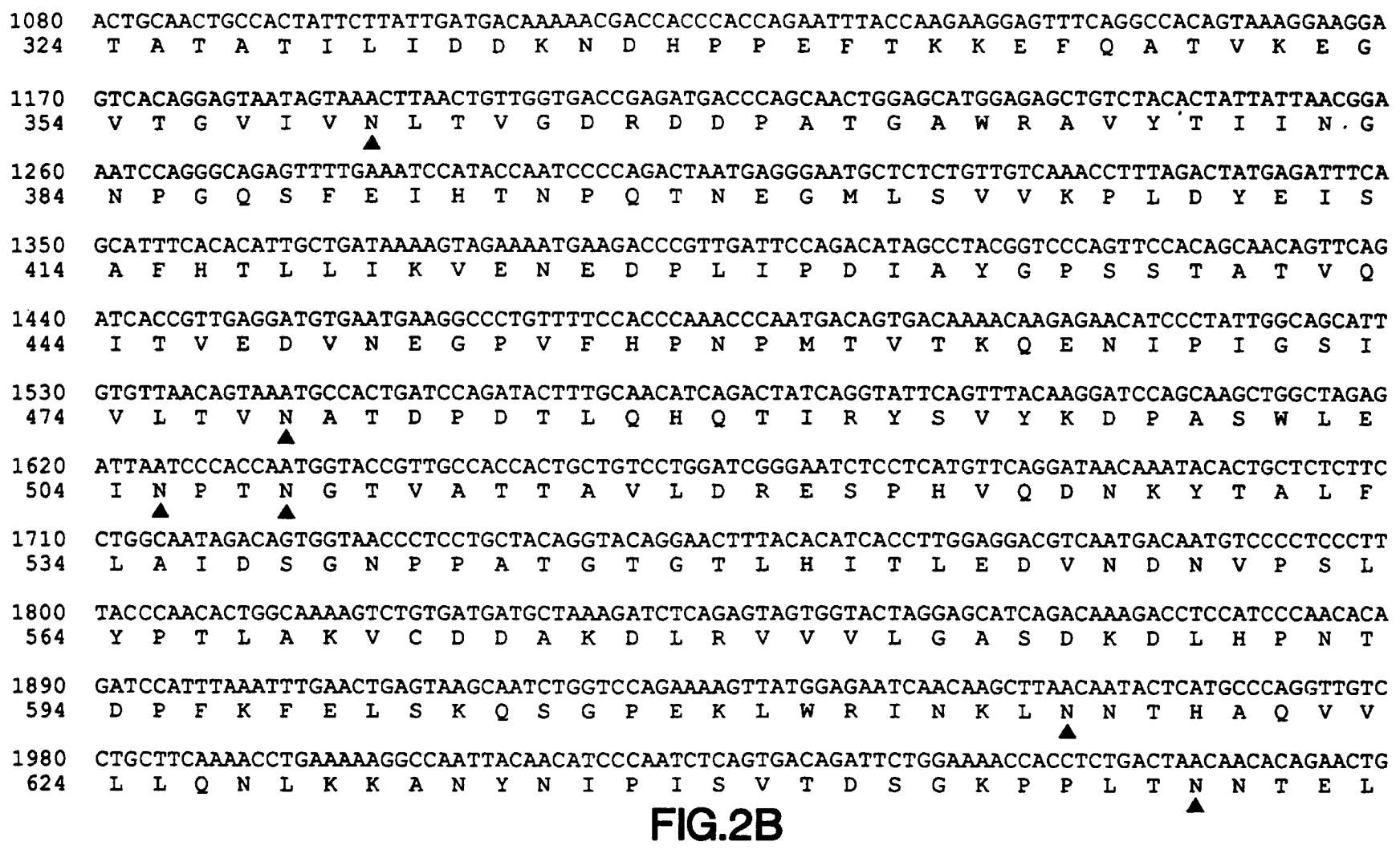

Alternatively, anti-T-cadherin antibodies can be prepared by immunizing an animal with synthetic peptides or recombinant protein fragments prepared from the sequence shown in FIGS. 2a to 2c (SEQ ID NO 2) and, FIGS. 2d to 2f (SEQ ID NO 4) as is well known in the art. Selection of anti-T-cadherin antibodies is performed as described above.

Monoclonal antibodies are prepared by immunizing an animal with material containing T-cadherin or synthetic peptides or recombinant protein fragments thereof, followed by isolating antibody-producing hybridoma cells, as is well known in the art. (See, for example, Harlow and Lane, ANTIBODIES: A LABORATORY MANUAL, Cold Spring Harbor, 1988, and the references cited therein, all which are incorporated herein by reference.) Anti-T-cadherin antibodies are selected by performing immunofluorescence analysis of tissue sections where T-cadherin is localized. The identification of antibodies is confirmed by immunoblotting and inmunoprecipitation which reveals the predominant 90 kD polypeptide described above. The appropriate hybridoma is reactive with purified T-cadherin or T-cadherin fragments. T-cadherin fragments can be prepared by expressing the T-cadherin cDNAs shown in FIGS. 2a to 2c (SEQ ID NO 1) and, FIGS 2d to 2f (SEQ ID NO 3) in a prokaryotic or eukaryotic expression vector as described above.

Methods of detecting T-cadherin in a subject are also provided. T-cadherin can be detected in a cell sample by using immunological techniques such as labeled antibodies. Such methods including the choice of label are known to those ordinarily skilled in the art. (Harlow and Lane, Supra). Briefly a subject's tissue sample is exposed first to an antibody specific for T-cadherin. After binding of the antibody, a second antibody, appropriately labeled and specific for the anti-T-cadherin antibody, is exposed to the sample previously incubated with the T-cadherin antibody. The secondary antibody can then be visualized or quantitated and the presence of T-cadherin detected. The invention provides a method of inhibiting tumor growth by inhibiting vascularization of the tumor. Treatment of the tumor with anti-T-cadherin antibodies reduces T-cadherin expression and the amount of vascularization.

The invention also provides a method of repairing traumatized neurons of a subject, including trauma due to stroke or injury. Administration of T-cadherin in the region of the traumatized neurons may influence neurons to regrow their axons and guide the axons to reinnervate their target cells.

The following examples are intended to illustrate but not limit the invention. While they are typical of those that might be used, other procedures known to those skilled in the art may alternatively be employed.

EXAMPLE I

Isolation of T-Cadherin

T-cadherin was identified as a concanavalin A-binding glycoprotein in the detergent-resistant membrane skeleton of chicken sympathetic neurons and embryo brain. The membrane skeleton was isolated as a non-ionic detergent resistant polypeptide complex was isolated in buffer A (10 mM Tris/HCl, pH 7.6, 2 mM $CaCl_2$ 5% Nonident P40, 2 mM dithiothreitol, 1 mM phenylmethylsulfonyl fluoride, 50 $\mu$M leupeptin, 5 $\mu$M pepstatin, 4 ng/ml aprotinin) from 13–16 day old chick embryo brains. The 90 kD fragment of T-cadherin was separated from the complex by preparative SDS gel electrophoresis (Laemmli, Nature 227:680–685 (1970)) as described above. Next to contactin, a 130 kD cell adhesion molecule of the immunoglobulin supergene family, T-cadherin is the major concanavalin A-binding glycoprotein of the complex (Ranscht et al., J. Cell Biol. 99:1803–18113 (1984)). The migration of T-cadherin on SDS-PAGE gels under reducing and non-reducing conditions is closely similar, suggesting that few or no intrachain disulfide bonds are present. Protein complexes containing T-cadherin, contactin, actin and approximately 15 other polypeptides were enriched by differential centrifugation and ion-exchange chromatography. The isolated protein complexes resist extraction with a variety of detergents in different salt conditions; thus, the individual components can only be dissociated from the complexes under denaturing conditions. T-cadherin can be purified by SDS preparative gel electrophoresis with a yield of approximately 50 $\mu$g from 50 g starting material.

EXAMPLE II

Protein Microsequencing

Proteins contained in brain polypeptide complex (BPC) were separated by preparative SDS-PAGE and electrophoretically transferred to a polyvinylidene difluoride membrane (Millipore, Burlington, Mass.) by methods well known to those skilled in the art. The 90 kD T-cadherin polypeptide was identified by staining the transferred proteins with Coomassie Brilliant Blue R250, excised and sequenced directly. Transfer conditions and processing were as described by Matsudaira, P., J. Biol. Chem. 262:10035–10038 (1987).

EXAMPLE III

Generation and Affinity Purification of Anti-T-Cadherin Antiserum

The detergent-resistant polypeptide complex was separated into its individual components by preparative SDS- PAGE gel electrophoresis. The 90 kD T-cadherin fragment was excised from several Coomassie-blue stained gels, electroeluted and desalted on exocellulose GF5 (Pierce, Rockford, Ill.). A New Zealand white rabbit was immunized by intramuscular and subcutaneous injections of 100 $\mu$g 90 kD T-cadherin polypeptide in Freund's complete adjuvant (1:1). The rabbit was boosted three times in four week intervals with an identical amount of protein in Freund's incomplete adjuvant. Final boosts were intravenous with 50–100 $\mu$g protein in phosphate-buffered saline (PBS). Blood was collected 7–10 days after the injections. The antiserum was absorbed on bovine liver acetone powder.

For some experiments, affinity purified antiserum was used. Affinity purification was achieved with T-cadherin immobilized by electrophoretic transfer onto polyvinylidene membranes (Millipore). The polypeptide complex was separated by SDS-PAGE and transferred to polyvinylidene membranes (Towbin et al., Proc. Natl. Acad. Sci. USA 76:356–375 (1979)). Proteins on the transfer were detected by staining with 1% amido black in methanol:acetic acid:water (20:10:70). The 90 kD T-cadherin peptide band was excised from the membrane and blocked for 30–60 minutes with 4% non-fat dry milk in TBST (10 mM Tris/HCl pH 8.0, 150 mM NaCl and 0.05% Tween 20). The T-cadherin strips were incubated with anti-T-cadherin antiserum (1:50 in TBST) for 2 hours at room temperature. Following washes in TBST, bound anti-T-cadherin antiserum was eluted from the strips with 600 $\mu$l 0.1M glycine, pH 2.5 for 5 minutes and neutralized immediately. The procedure was repeated five times to obtain sufficient quantities of purified antibody.

Figure 4:
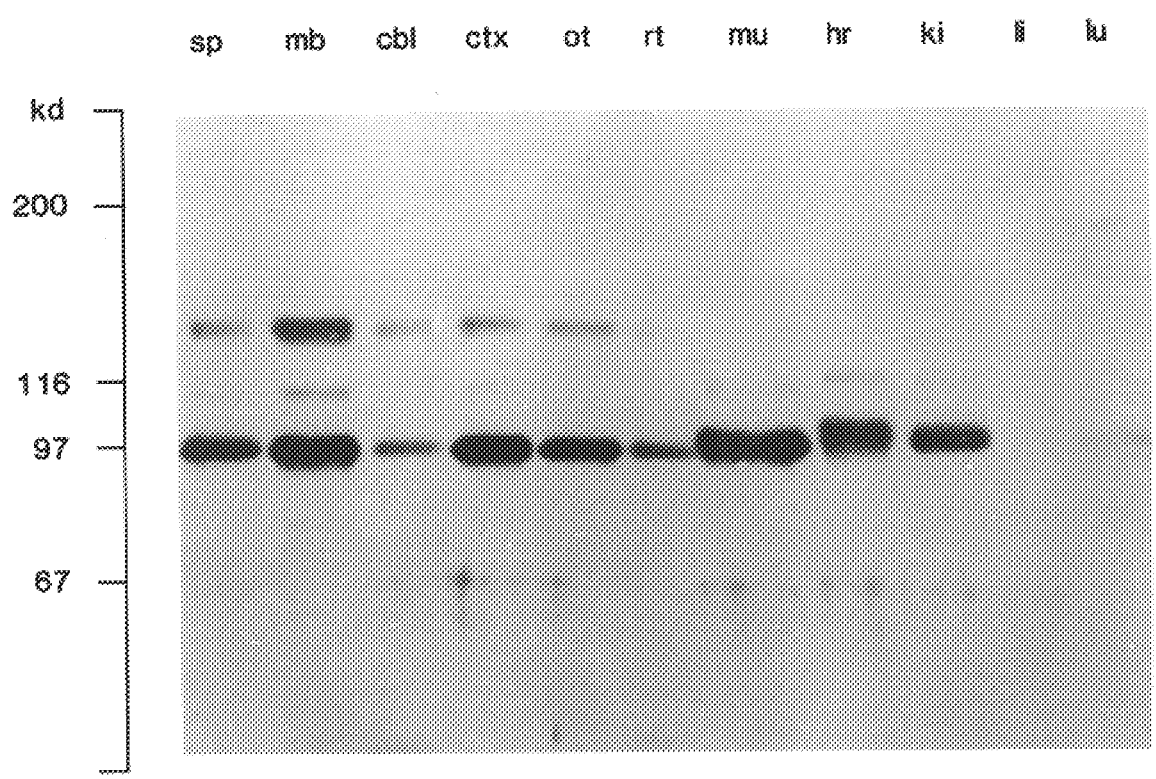
FIG. 4 is an immunoblot of various tissues isolated from 3 day old chicks using antiserum to T-cadherin. Polypeptides having an $M_r$ of 90, 110 and 120 kD are detected in neural tissues whereas only the 90 and 110 kD polypeptides are detected in non-neural tissues. Lane 1, spinal cord; lane 2, midbrain; lane 3, cerebellum; lane 4, cortex; lane 5, optic tectum; lane 6, retina; lane 7, muscle; lane 8, heart; lane 9, kidney; lane 10, liver; lane 11, lung.
Figure 5A:
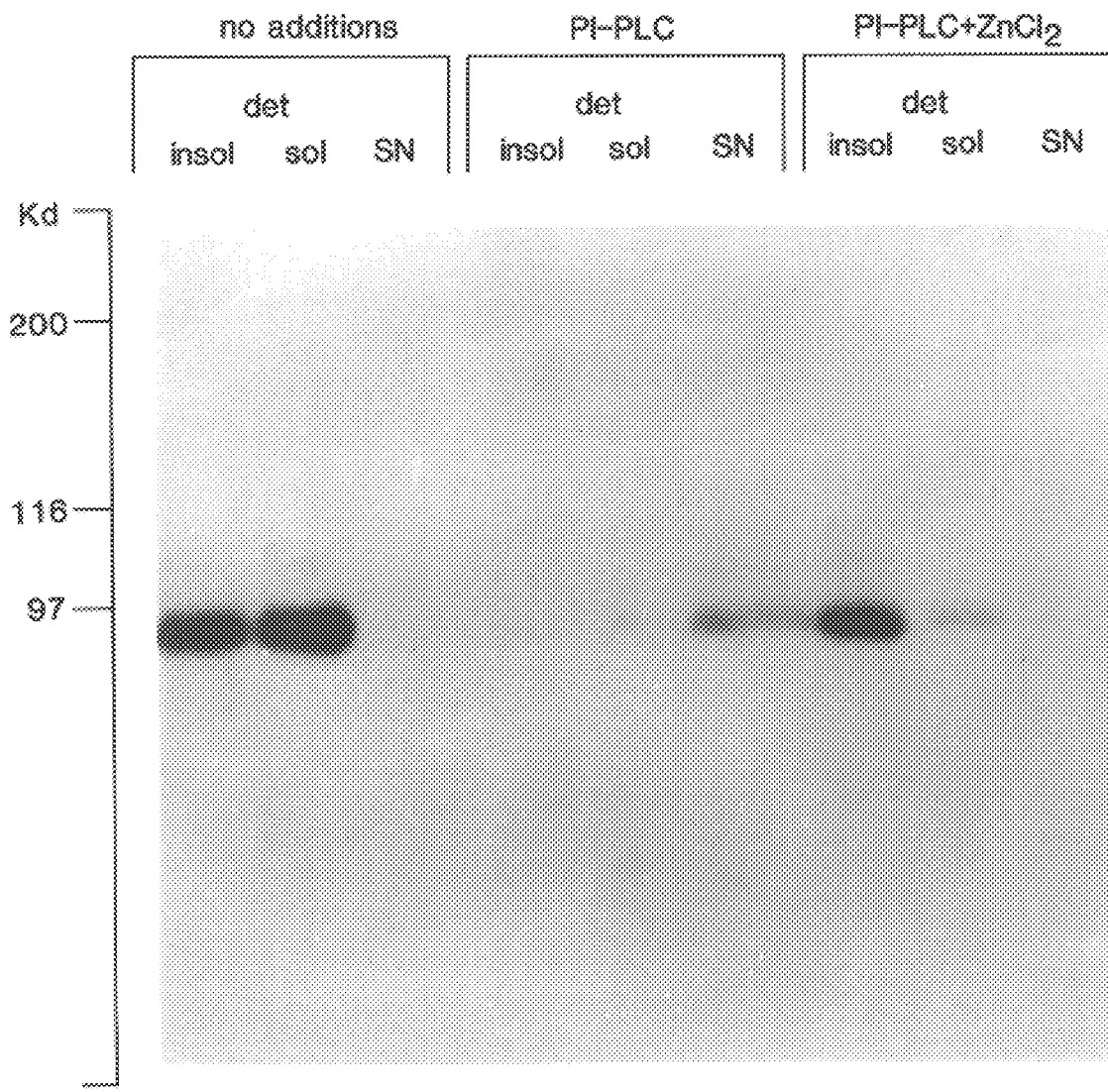
FIG. 5a shows the release of T-cadherin from cultured neurons following phosphotidylinositol phospholipase C (PI-PLC) treatment by Western Blotting with T-cadherin antiserum. T-cadherin is released into the supernatant after PI-PLC treatment (lane 6). The release is blocked by treatment with $ZnCl_2$ (lane 9).
Figure 5B:
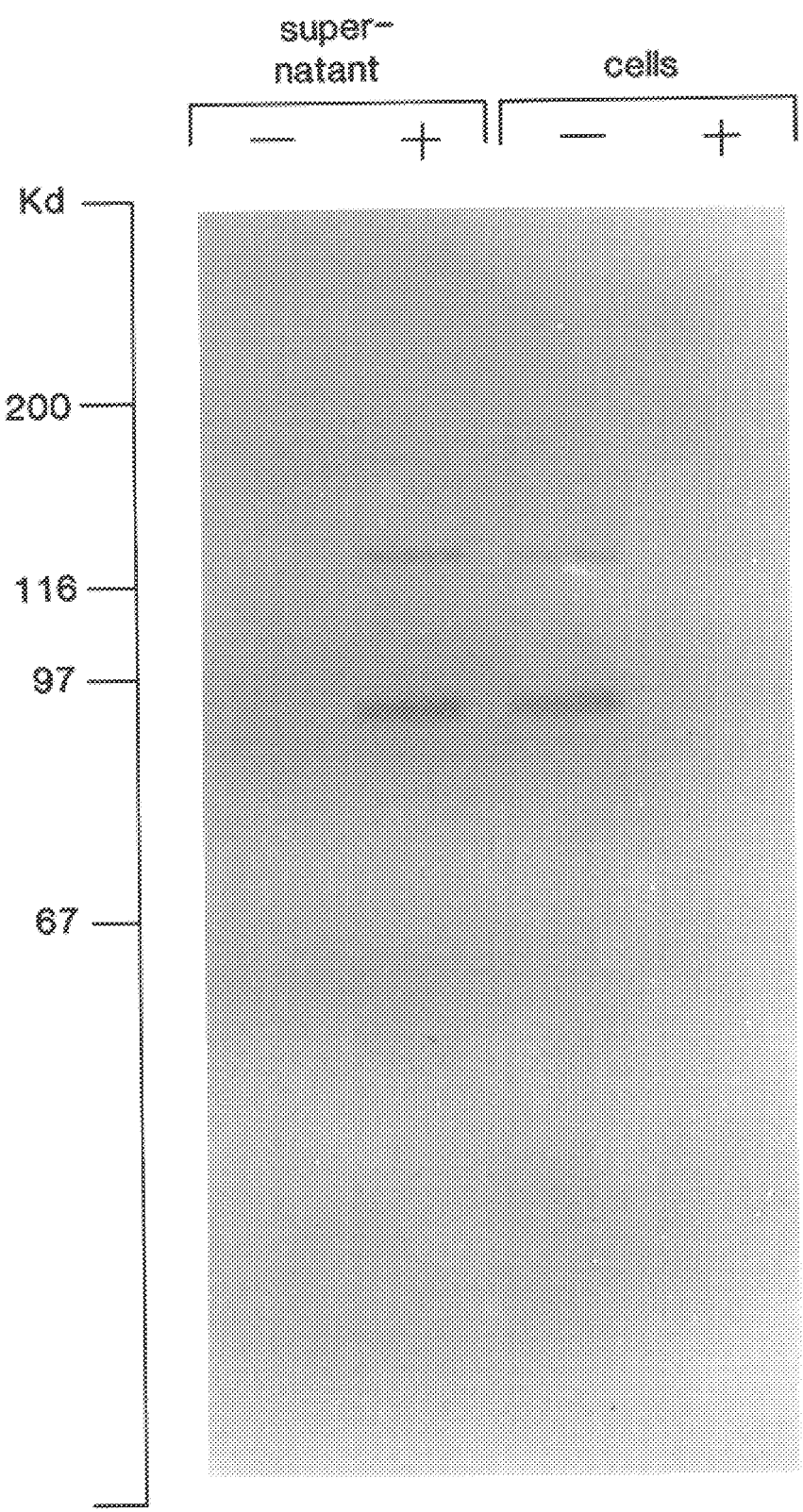
FIG. 5b is an immunoprecipitation of $^3H$-ethanolamine labeled T-cadherin following release from cultured neurons with PI-PLC. Two polypeptides of $M_r$ 90 and 120 kD are released by PI-PLC and are precipitated with T-cadherin antiserum (lane 2).
Figure 6:
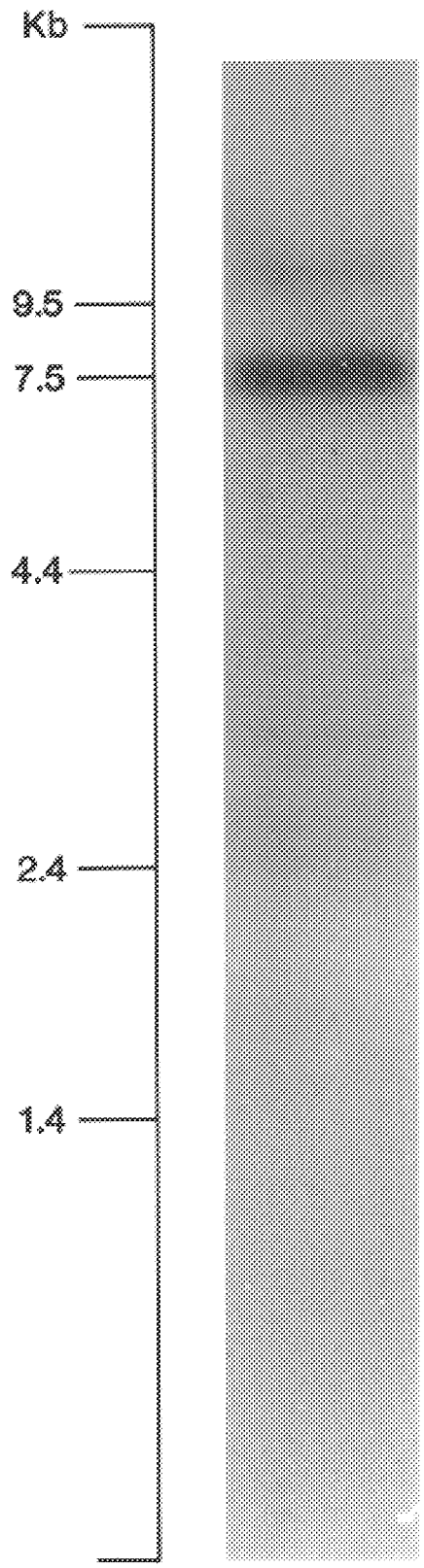
FIG. 6 is an RNA blot of brain tissue probed with a T-cadherin cDNA portion corresponding to the T-cadherin 1 Eco RI-Pst I restriction fragment (1.76 kb). The probe detects two mRNA species of 7.5 and 9.5 kb.
Figure 7A:
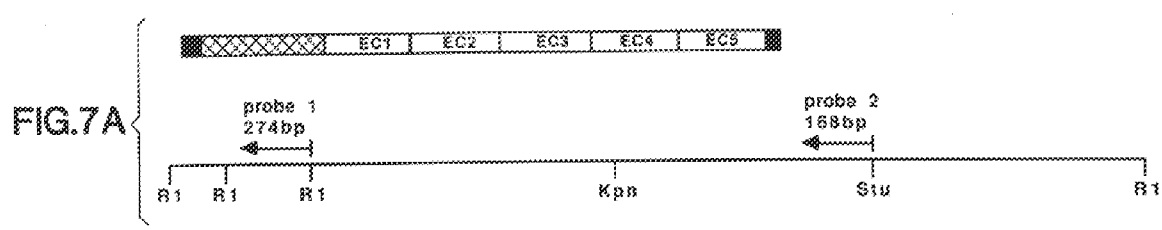
FIGS. 7a and 7b show a RNase protection assay of T-cadherin MRNA. Samples are BR=brain, M=muscle, LI=liver, H=heart, K=kidney, LU=lung, RT=retina from hatched chickens. N=cultured sympathetic neurons as in Example 5. Spinal cord H/H stage 37 and 24. Spinal cord H/H stage 24 separated into D=dorsal, V=ventral and FP=floor plate region. SOM=somites.
Figure 7B:
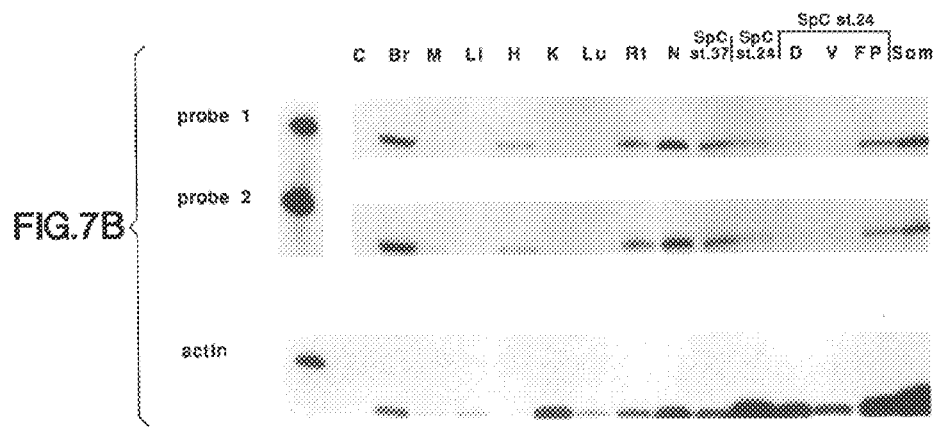

On immunoblots of nervous tissue homogenates, this antiserum recognized a major protein component of 90 kD. In addition, protein species of 110 and 120 kD were detected with the antiserum (FIG. 4). The 110 kD polypeptide is likely to represent T-cadherin with the preptide, since both the 90 and the 110 kD species are obtained after transfection of COS-cells with T-cadherin cDNAs. The 120 kD protein is immunoprecipitated with the T-cadherin antiserum after $^3$H-ethanolamine labelling indicating that this protein is also GPI-linked to the membrane. Therefore, the 120 kD polypeptide is likely to be a nervous system specific form of T-cadherin. In contrast to neural tissue, the T-cadherin antiserum recognizes only the 90 and 110 kD protein species in non-neural tissue samples. Microsequencing of the 17 $NH_2$ terminal amino acids of the 90 kD protein and mapping of this sequence to the protein conceptually translated from the cDNA sequence indicates that the 90 kD protein is a fragment of T-cadherin that starts at amino acid residue 117 (FIGS. 2a to 2c and FIGS 2d to 2f) and excludes the signal and the prepeptide.

EXAMPLE IV

Immunoblotting Procedures

Various tissues including brain, retina, muscle, liver, heart and kidney were homogenized in buffer A (see EXAMPLE I) and separated by SDS-PAGE. Separated proteins were electrophoretically transferred to a polyvinylidene difluoride membrane. Marker lanes were stained separately with 0.1% amido black in methanol:acetic acid:$H_2O$ (20:10:70) and destained in the identical solution without the dye. For immunoblotting, non-specific binding sites were blocked as described above and the blots incubated for 60 minutes with anti-T-cadherin antiserum (1:150 for both the non-purified and the purified antiserum). Following washes in TBST, bound antibodies were detected with 1 $\mu$Ci/ml $^{125}$I goat anti-rabbit immunoglobulin (ICN Biochemicals Inc., Costa Mesa, Calif.) followed by autoradiography using Cronex Lightning Plus screens. In some experiments the blots were reacted using alkaline phosphatase conjugated goat anti-rabbit immunoglobulin and 5-bromo-4-chloro-3-indolyl-phosphate (BCIP) and nitro blue tetrazolium (NBT) as enzyme substrates (Protoblot, Progema, Madison, Wis.) or the ECL Western Blotting detection system (Amersham Corporation, Arlington Heights, Ill.).

EXAMPLE V

Phospholipase Digestion of Cultured Sympathetic Neurons

Sympathetic ganglia were dissected from 10 day old chicken embryos in L15 medium. The ganglia were dissociated after a 30 minute digestion with 0.25% trypsin in PBS and plated in L15 culture medium onto culture dishes coated with laminin (5 $\mu$g/ml, Telios Pharmaceuticals, Inc., La Jolla, Calif.) at a density of 1.4–1.8×10$^6$ cells/60 mm culture dish. The culture medium was supplemented with 10% dialyzed fetal calf serum, 0.5% methylcellulose, 2 mM glutamine, 0.6 g/l glucose, nerve growth factor and antibiotics. Extensive nerve fiber growth was observed after a 48-hour culture period.

For phospholipase digestion, 48 hour cultures were extensively washed with PBS. The cultures were incubated for 60 minutes at 37° C. with 5 U/ml phosphoinositol specific phospholipase C (PI-PLC, a gift from Dr. M. Low, Columbia University, N.Y.) in PLC-buffer (PBS containing 1 mM phenylmethylsulfonyl fluoride, 50 $\mu$M leupeptin, 5 $\mu$M pepstatin, 4 ng/ml aprotinin and 5 $\mu$g/ml $\alpha_2$-macroglobulin). The released material was collected, freed of cellular debris by centrifugation and concentrated 10 fold by ultrafiltration. The neuronal cells were peeled off the laminin substrate, washed with PLC-buffer and homogenized in 200 $\mu$l H-buffer (10 mM Tris/HCl, pH 7.5, 2 mM $CaCl_2$, 2% Nonidet-P40, 0.25 mM dithiothreitol and protease inhibitors phenylmethylsulfonyl fluoride, leupeptin, pepstatin, aprotinin as above). Detergent-soluble and insoluble material was separated by centrifugation at 100,000 g for 45 minutes at 4° C. Control samples received PLC-buffer only; in two experiments 5 mM $ZnCl_2$ was included during the digestion with the phosphoinositol specific phospholipase.

Released and cellular components of the PI-PLC treated cultures were separated by SDS-PAGE and analyzed on Western blots. In control samples (no additions), T-cadherin was found in the detergent soluble and insoluble fraction of the cells. T-cadherin was not detectable in the supernatant after the 60 minute incubation period. In contrast, when cells were treated with PI-PLC, essentially all of the T-cadherin was released into the supernatant after 60 minutes. This release was blocked by $ZnCl_2$ treatment of cells, an inhibiter of PI-PLC.

T-cadherin is secreted into the culture medium over longer culture periods ($\geq$18 hours). In the culture medium, T-cadherin appears in a highly soluble form as well as in association with an insoluble complex of extracellular matrix components that is pelleted by centrifugation of the culture supernatant at 100,000 g for 3 hours.

EXAMPLE VI

Labeling with $^3$H-Ethanolamine and Fluorography

Cultures of sympathetic neurons were grown for 48 hours and then labeled for 18 hours with $^3$H-ethanolamine (100 $\mu$Ci/ml; specific activity 19–24 Ci/mmol (Amersham, Arlington Heights, Ill.) in supplemented LIS medium. Labeled cultures were either treated with phosphatidylinositol-specific phospholipase C as described below or processed immediately for analysis. The cells were lysed in H-buffer (10 mM Tris/HCl, pH 7.5, 2 mM $CaCl_2$, 2% Nonidet-P40, 0.25 mM dithiothreitol and protease inhibitors: 1 mm phenylmethyl-sulfonyl fluoride, 50 mM leupeptin, 5 μM pepstatin, 4 ng/ml aprotinin) and the proteins separated by SDS-PAGE. Gels were stained with Coomassie Brilliant Blue R250, destained and equilibrated in water. For fluorography processing, the gels were equilibrated in dimethylsulfoxide (DMSO) for 30 minutes and then treated for 60 minutes with 20% 2,5-Diphenyloxazole (PPO) in DMSO. Gels were dried after extensive washing in water and exposed for 4–12 weeks with presensitized Kodak XAR-5 film.

EXAMPLE VII

Immunoprecipitation

T-cadherin was immunoprecipitated from $^3$H-ethanolamine labeled sympathetic neuronal cultures. Following the labeling period, as in EXAMPLE IV, the cultures were thoroughly washed and lysed with 150 mM NaCl in 10 mM Tris/HCl, pH 7.0, 150 mM NaCl, 1% Deoxycholate, 1% Nonident-P40, 0.2% sodium dodecylsulfate, 1 mm phenylmethylsulfonyl fluoride, 50 μM leupeptin, 5 μM pepstatin, 4 μg/ml aprotinin and 1 mM dithiothreitol. The lysate was cleared by centrifugation at 16,000 g for 30 minutes at 4° C. T-cadherin was complexed from the soluble protein pool with anti-T-cadherin antiserum (1:50) for 60 minutes at 4° C. The antigen/antibody complexes were precipitated with fixed staphylococcus aureus (Pansorbin, Calbiochem, La Jolla, Calif.). Precipitates were washed by centrifugation at 3000 g for 20 minutes through layers of 5%, 10% and 20% sucrose. The precipitates were resuspended in SDS-PAGE loading buffer (Maniatis et al., Supra) and analyzed by SDS-PAGE followed by fluorography as described above.

EXAMPLE VIII

Immunocytochemistry

The localization of T-cadherin was examined using indirect immunofluorescence techniques. Chicken embryos between day 2 and 8 of embryonic development were staged using the criteria of Hamburger and Hamilton (J. Morph. 88:49–192 (1951)) (H & H). The animals were fixed by immersion into PLPA-fixative (100 mM Na-periodate, 75 mM lysine and 3% paraformaldehyde in PBS) or 4% paraformaldehyde alone for 1–3 hours depending on their size. The tissue was kryoprotected by successive immersion into 5% and 10% sucrose in PBS for 8–12 hours, embedded in Tissue-Tek (Miles Laboratories Elkhart, Ind.) and frozen at −70° C. Serial sections of 15 μm thickness were cut on a kryostat and collected on gelatine/chromalum (1% gelatine/ 0.4% chromalum) coated slides. Sections were stained for 3–4 hours at room temperature with rabbit anti-T-cadherin (1:100). Bound antibodies were detected with FITC or TRITC conjugated goat anti-rabbit IgG (1:150, Cappel Laboratories, Inc., Westchester, Pa.) Antibody dilutions were in GST-PBS (10% normal goat serum and 0.02% Triton-X100 in PBS), washes after each incubation step with PBS only. Stained sections were mounted with immunomount containing 2% 1,4-Diazabicyclo- (2.2.2)-octane (Aldrich, [Milwaukee, Wis.) to prevent rapid bleaching.

In the developing spinal cord at stage 20 (FIG. 8d) (H & H), motor neurons are in their early phase of differentiation and axon extension. Commissural axons that project from dorsolateral and dorsomedial sites to the floor plate region have commenced to extend processes towards the floor plate that serves as their intermediate target. At this stage of development, T-cadherin was found to be expressed on the cell bodies and nerve fibers of motor neurons and on ventral neuroepithelial cells including the floor plate. Other neurons or their precursors were not stained at this early stage.

At stage 24 (FIG. 8e), the majority of commissural axons have crossed the ventral midline of the spinal cord projecting through the ventral ridge of the floor plate. At this stage, the staining intensity of T-cadherin was strikingly increased in the floor plate region. Comparatively little staining was detected in other areas of the neural tube. The pattern of T-cadherin expression includes the floor plate epithelial cells as in previous stages and a segment of the commissural axons as they cross this area. This pattern suggests that commissural axons are stained by anti-T-cadherin only in the segment in contact with the floor plate. The expression in the floor plate region was transient, since in older animals little staining or none can be detected in the floor plate area.

Figure 8A:
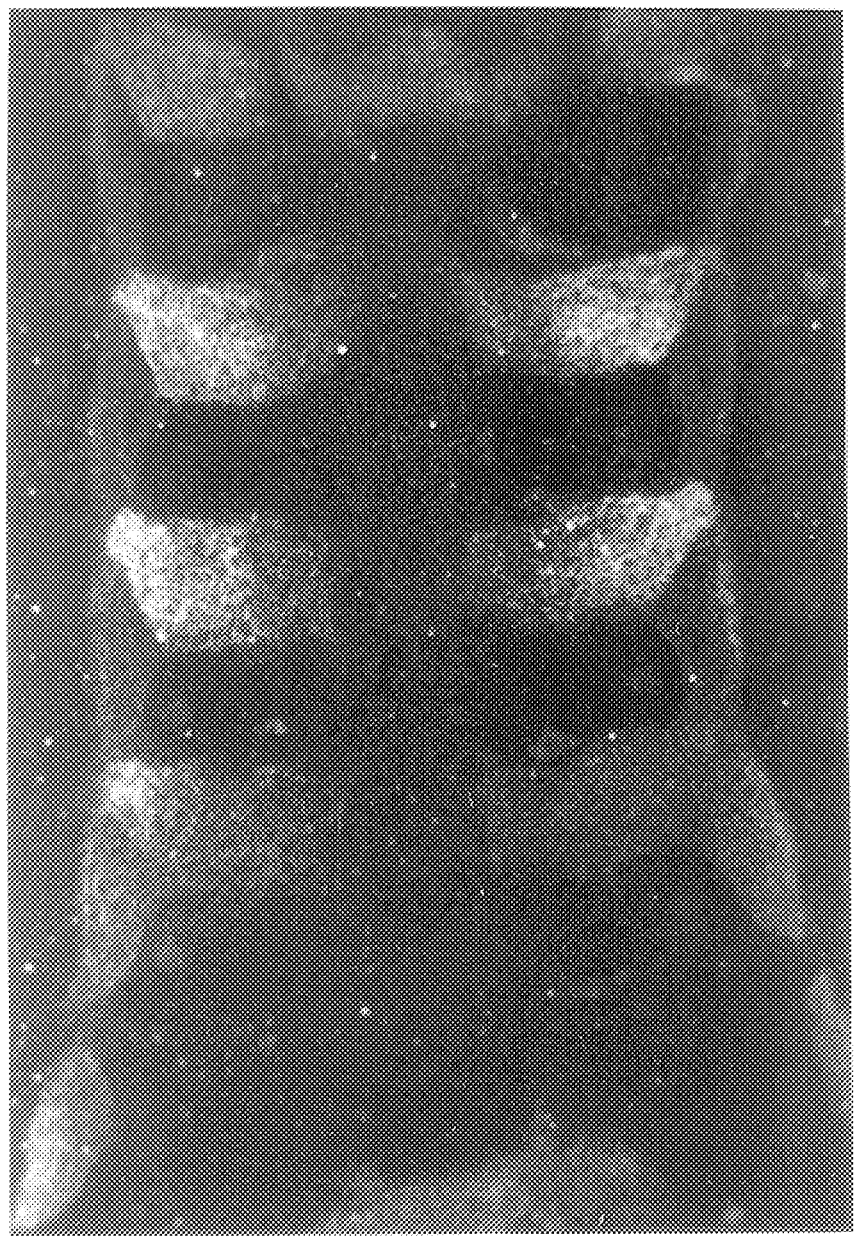
FIGS. 8A–H are immunohistochemistry analysis of T-cadherin expression in the developing nervous system. The tissues examined are: (8a, 8b, 8c) somites H/H stage 23; (8d, 8e, 8f) developing spinal cord, (8d), H/H stage 20, (8e), H/H stage 24 and (8f), H/H stage 32; (8gf) blood vessel; and (8h) muscle.
Figure 8B:
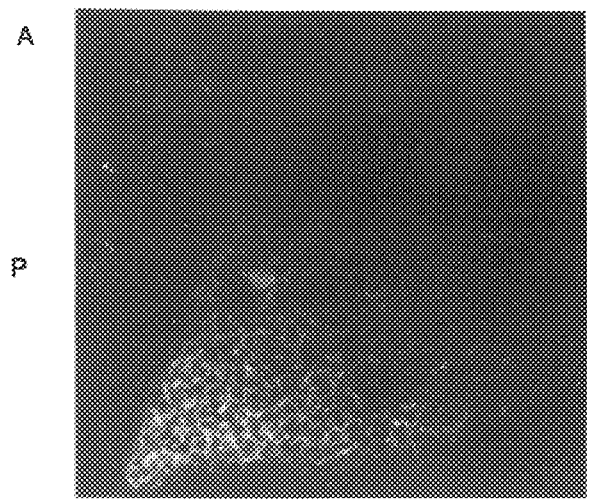
Figure 8C:
Figure 8D:
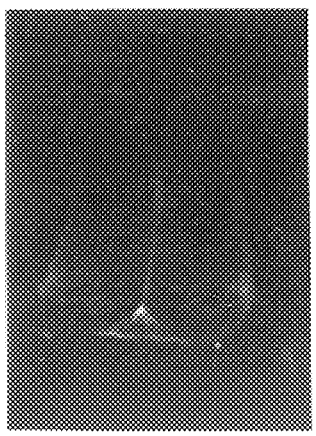
Figure 8E:
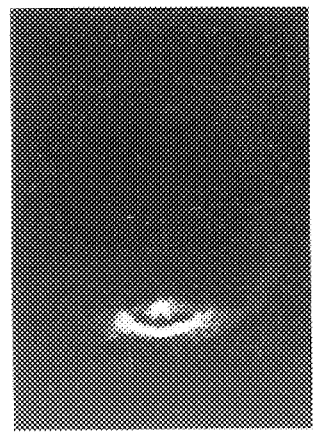
Figure 8F:
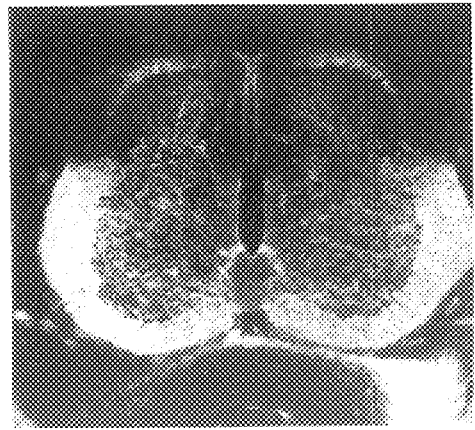
Figure 8G:
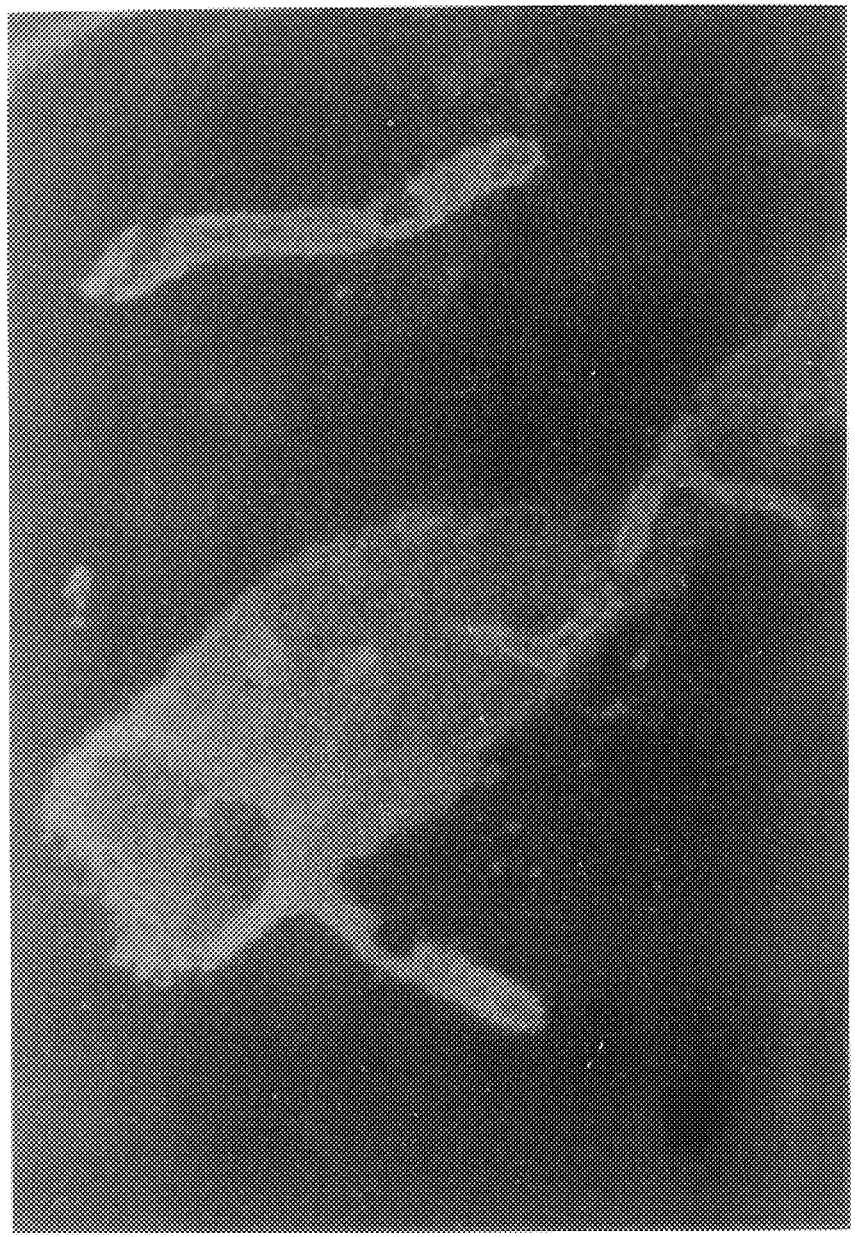
Figure 8H:
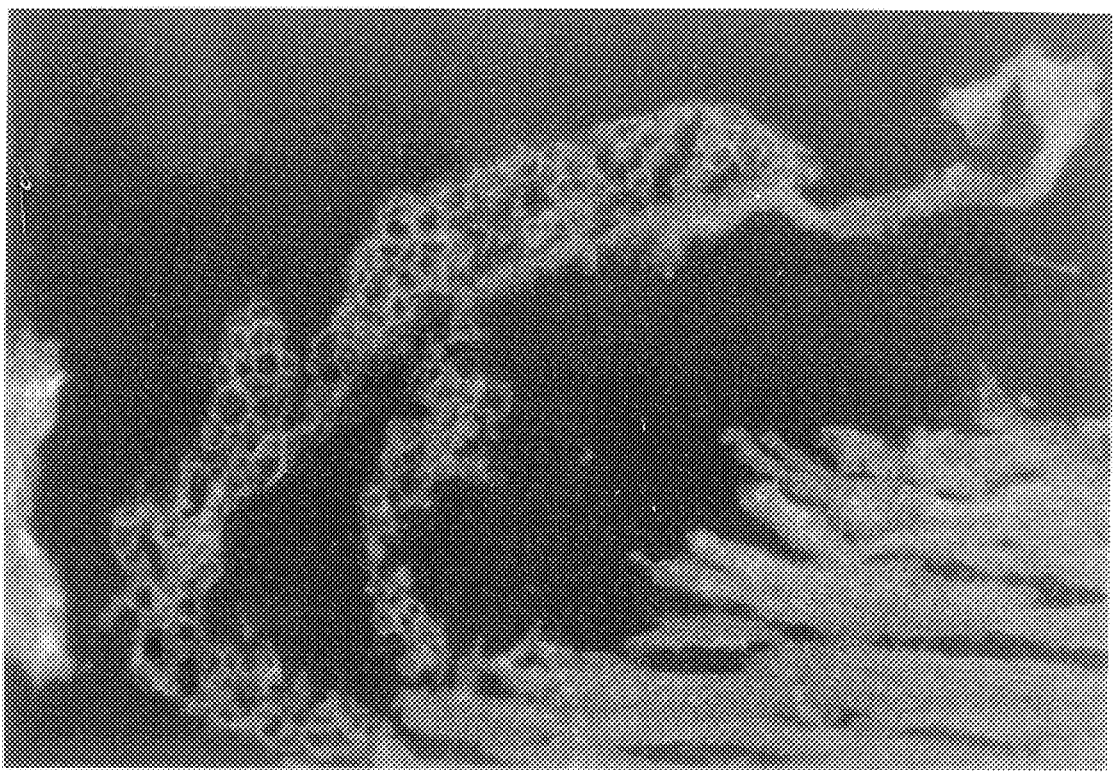

Motor neurons select as their intermediate targets the anterior region of the somitic sclerotome (Keynes and Stern, Nature 310:786–789 (1984)), thus establishing a segmental pattern of nerve projections. In coronal sections of stage 22–23 chicken embryos, T-cadherin was expressed in a striking segmental pattern on the surface of posterior somite cells, (FIG. 8a). The spinal nerve fascicles crossing the anterior somite regions were identified in an adjacent section with anti-contactin antibodies (FIG. 8b). The segmental pattern of T-cadherin expression was observed as early as neural crest cells enter the somite regions.

EXAMPLE IX

Identification of cDNA Clones Encoding T-cadherin

A cDNA library generated from embryonic day 13 chicken brain (Ranscht, J. Cell Biol. 107:1561–1573 (1988)) was screened for cDNA clones encoding T-cadherin. Nitrocellulose replica filters of a lambda gt 11 expression library from embryonal day 13 chick brain were screened with affinity purified anti-T-cadherin antiserum (1:40). Screening was essentially as described by Maniatis, incorporated herein by reference. Alkaline phosphatase conjugated goat anti-rabbit immunoglobulin and 5-bromo-4-chloro-3-indolyl phosphate (BCIP) and nitro blue tetrazolium (NBT) substrates (Protoblot, Progema) were used as a detection system. In the initial screening one clone was isolated from $7 \times 10^5$ amplified and $8 \times 10^4$ unamplified recombinants. This clone represented a true T-cadherin transcript by two criteria:

1) The CDNA encoded a fusion protein that was recognized by anti-T-cadherin antiserum. Affinity purification of the antiserum on recombinant fusion protein selected antibodies specific for the 90 kd protein in brain homogenates on Western blots. Moreover, the affinity purified antiserum stained in indirect immunofluorescence on sections of stage 22–23 chick embryos posterior somite segments.

2) Conclusive evidence that the selected CDNA represented a T-cadherin transcript was obtained by comparison of the conceptually translated cDNA sequence with the amino acid sequence obtained by microsequencing of the $NH_2$-terminus of the 90 kD protein. The 17 $NH_2$-terminal amino acids of the 90 kD polypeptide mapped to amino acids 117 to 133 in the open reading frame of the protein conceptually translated from the cDNA sequence (See FIGS. 2a to 2c and FIGS 2d to 2f) (SEQ ID NO 1 to 4).

EXAMPLE X

Isolation of Additional T-cadherin cDNA Clones

Sixteen additional cDNA clones for T-cadherin were isolated by screening both lambda gt 10 (amplified) and lambda gt 11 (unamplified) chick brain libraries with T-cad-2 restriction fragments that were labeled by nick translation (Maniatis et al., Supra; kit from Bethesda Research Laboratories (Gaithersburg, Md.). The restriction fragments constituted nucleotides 440–1559 of the initially isolated clone and included the coding sequences encoding the $NH_2$-terminus of the 90 kD protein. Phage plaques were transferred in duplex to Hybond nylon membranes (Amersham, Arlington Heights, Ill.). The filters were processed successively through 1.5M NaCl/0.5M NaOH for 2 minutes, 3M Na-acetate, pH 5.2 for 5 minutes and 20×SSPE (3M NaCl, 0.2M $NaH_2PO_4 \times H_2O$, 0.02M $Na_2$ EDTA, pH 7.4), dried and baked for 60 minutes in a vacuum oven. Prehybridization was at 42° C. in 50% deionized formamide, 5× SSPE, 1× Denhardts and 100 µg/ml salmon sperm DNA for 2–4 hours. Hybridization was overnight under identical conditions with the probe at $2 \times 10^6$ cpm/filter. The filters were washed under high stringency conditions (0.2×SSPE/ 0.2% SDS at 68° C.) and exposed overnight to Kodak XAR-5 film.

All clones shared restriction sites within their internal nucleotide sequence, but varied in length from 1 to 3.8 kb. EcoR1 restriction fragments of all clones were subcloned into the Bluescript KS+vector (Stratagene, La Jolla, Calif.) and used for nucleotide sequence determination using a double stranded DNA as a template. Sequence over internal EcoR1 sites was obtained from lambda CDNA templates. The nucleotide sequence of clone 266 (=T-cad 1), one of the longest cDNA clones (3.8 kb) and of CDNA 1212 (=T-cad 2) are shown in FIGS. 2a to 2c and FIGS. 2d to 2f.

EXAMPLE XI

RNA Isolation

Total cellular RNA was isolated from hatched chicks by the guanidinium isothiocyanate method (Maniatis et al., Supra). Briefly, the tissues were homogenized on ice in 4 to 6 mls of 4M guanidinium thiocyanate (GTC) buffer per gram of tissue (94.4 g GTC, 1.67 ml 3M sodium acetate, pH 6.0, 0.5% sarkosyl, 200 µl antifoam A, 500 µl 1 NaOH, to 200 ml with DEPC treated dd $H_2O$, 0.1M final concentration of 2-mercaptoethanol should be added just prior to use). The homogenate is layered onto 4 to 5 mls of 5.7M CsCl solution in a SW 40 centrifuge tube (Beckman, Carlsbad, Calif.). The CsCl solution is prepared in the following manner: 95.97 g CsCl, 0.83 mls 3M sodium acetate pH 6.0, to 100 mls with DEPC-dd $H_2O$ and filter sterilize. The tubes are balanced with GTC buffer and the samples are centrifuged at 32,000 rpm for 18 hours using an ultracentrifuge (Sorvall, Newtown, Conn.). Following centrifugation, the GTC buffer and CsCl solution is aspirated off leaving about 1 ml of CsCl solution covering the RNA pellet. The walls of the tube are rinsed with 1 to 2 mls of GTC buffer and the buffer, including CsCl layer, is carefully removed. The tubes are cut 1–2 cm from the bottom using a hot razor blade and the RNA pellets are rinsed with 400 µl of 20° C. ethanol, dried and resuspended in Tris-EDTA (TE; 10 mM Tris-Hcl, pH 7.6, 1 mM EDTA). The resuspended RNA is purified by extracting twice with an equal volume of phenol/chloroform followed by ethanol precipitation and washing as described above. RNA was quantitated by absorbance at 260 nm ($OD_{260}$ of 1=50 ml/ml). Purity was checked by determining the absorbance ratio at 260 nm compared to the absorbance at 280 nm (OD 260/280≧2.0 for RNA). The RNA samples were stored as ethanol precipitates at 70° C. until further use. From tissues of early developing chicken embryos, RNA was prepared by lithium precipitation as described in Maniatis, Supra. When probed with T-cadherin cDNA, two transcripts of approximately 9.5 and 7.5 kb were detected.

EXAMPLE XII

RNase Protection

RNA transcripts encoding the T-cadherin prepeptide and 3' untranslated regions were generated by in vitro transcription of T-cadherin cDNA. The template for the prepeptide probe (common to T-cad 1 and T-cad 2) was a 274 bp EcoR1 restriction fragment (FIGS. 2d, e, f) from lambda gt 11 T-cad 2 cloned into Bluescript $KS^+$. The fragment was linearized by digestion with HindIII in the polylinker region. A specific 3' end probe of T-cad 1 was generated by removing 1.5 kb untranslated sequence from the extreme 3' end of clone T-cad 1 by restriction digestion with StuI/SmaI and religation of the blunt ends. A 168 bp template was obtained by linearizing T-cad 1 DNA with SfaI. A specific 3' end template for T-cad 2 was generated by cloning its 2.1 kb EcoR1 restriction fragment into Bluescript $KS^+$ and digestion of the cDNA fragment with Hpal. Chicken β-actin cDNA (kindly provided by Dr. D. Cleveland, Johns Hopkins University, Baltimore, Md.) was used as a control. The β-actin cDNA was digested with KpnI and HindIII and cloned into the SP72 transcription vector (Melton et al., Nucleic Acids Res. 13:7035–7056 (1984)). The DNA was linearized by digestion with PvuII. The templates were transcribed in anti-sense orientation in the presence of T7 RNA polymerase and $^{32}P$-rUTP under conditions described by Melton, Supra. Probes were purified on polyacrylamide gels. A 1% aliquot of the total probe was hybridized overnight in 80% formamide, 400 mM NaCl, 4 mM PIPES and 1 mM EDTA at 45° C. to 2–10 µg total RNA from various tissues. Non-hybridized RNA was digested with RNases A and T1 for 60 minutes at room temperature. RNA hybrids were separated on polyacrylamide gels and analyzed after exposure to Kodak XAR-5 film.

All tissues that show a protected fragment with the prepeptide probe, also showed a protected fragment with the 3' fragment, indicating that MRNA encoding the phosphoinositol linked form of T-cadherin exists in the tissues. Brain, heart, retina, cultured sympathetic neurons, stage 37 and 24 spinal cord (especially floor plate), and somites revealed protected fragments.

Although the invention has been described with reference to the presently preferred embodiment, it should be understood that various modifications can be made without departing from the spirit of the invention. Accordingly, the invention is limited only by the following claims.

I claim:

1. An antibody or fragment thereof specifically reactive with T-cadherin (SEQ ID NO:2 or SEQ ID NO:4), but not N-, E- or P-cadherin.

2. The antibody or fragment of claim 1, wherein the antibody is polyclonal.

3. The antibody or fragment of claim 1, wherein the antibody is monoclonal.

4. A method of obtaining an antibody specifically reactive with T-cadherin (SEQ ID NO:2 or SEQ ID NO:4), but not N-, E- or P-cadherin, comprising the steps of administering to an animal an immunogenic synthetic peptide or an immunogenic synthetic recombinant protein fragment having a partial amino acid sequence of T-cadherin (SEQ ID NO:2 or SEQ ID NO:4) and isolating from the animal's serum an antibody specifically reactive with T-cadherin, but not N-, E- or P-cadherin.

5. The method of claim 4, wherein the recombinant protein fragment is encoded by a partial nucleic acid sequence of T-cadherin as set forth in SEQ ID NO:1 or SEQ ID NO:3.

6. An antibody or fragment thereof obtained by administering to an animal an immunogenic synthetic peptide or an immunogenic synthetic recombinant protein fragment prepared from a partial sequence of T-cadherin (SEQ ID NO:2 or SEQ ID NO:4), wherein the antibody is specifically reactive with T-cadherin, but not N-, E- or P-cadherin.

7. The antibody or fragment of claim 6, wherein the recombinant protein fragment is encoded by a partial nucleic acid sequence of T-cadherin as set forth in SEQ ID NO:1 or SEQ ID NO:3.

8. The antibody or fragment of claim 6, wherein the antibody is polyclonal.

9. The antibody or fragment of claim 6, wherein the antibody is monoclonal.

* * * * *

UNITED STATES PATENT AND TRADEMARK OFFICE
CERTIFICATE OF CORRECTION

PATENT NO. : 5,863,804
DATED : January 26, 1999
INVENTOR(S) : Barbara Ranscht

It is certified that error appears in the above-identified patent and that said Letters Patent is hereby corrected as shown below:

Column 3,
Line 12, please replace "(8gf)" with -- (8g) --.

Column 4,
Line 3, after "2f" please insert -- (SEQ ID NOS 2 and 4) --.
Line 23, after "2a" please insert -- to 2c --.
Line 24, please replace "2b" with -- 2d to 2f --.

Column 9,
Line 1, please replace "LIS" with -- L15 --.

Column 10,
Line 61, please replace "CDNA" with -- cDNA --.

Column 11,
Line 39, please replace "CDNA" with -- cDNA --.
Line 41, please replace "CDNA" with -- cDNA --.

Column 12,
Line 13, please replace "70° C" with -- -70° C --.

Signed and Sealed this

Nineteenth Day of March, 2002

*Attest:*

JAMES E. ROGAN
*Director of the United States Patent and Trademark Office*

*Attesting Officer*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 3959 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 45..2181

( x i ) SEQUENCE DESCRIPTION: SEQ ID NO:1:

```
GAATTCCGAA TGAAAAGCC TCTGGTACGT TCTAGTCTGG CAAA ATG CAG CAC AAA             56
                                                Met Gln His Lys
                                                 1

ACT CAA CTT ACT CTG TCC TTT CTG CTG TCC CAG GTT CTG TTG CTT GCG           104
Thr Gln Leu Thr Leu Ser Phe Leu Leu Ser Gln Val Leu Leu Leu Ala
  5              10                 15                   20

TGT GCA GAA GAT TTA GAA TGC ACC CCT GGA TTC CAG CAA AAG GTT TTT           152
Cys Ala Glu Asp Leu Glu Cys Thr Pro Gly Phe Gln Gln Lys Val Phe
             25                 30                  35

TAT ATT GAA CAG CCA TTT GAA TTC ACA GAG GAC CAG CCA ATT CTG AAC           200
Tyr Ile Glu Gln Pro Phe Glu Phe Thr Glu Asp Gln Pro Ile Leu Asn
         40                 45                 50

CTG GTG TTT GAT GAC TGC AAG GGG AAT AAC AAA TTG AAC TTC GAA GTT           248
Leu Val Phe Asp Asp Cys Lys Gly Asn Asn Lys Leu Asn Phe Glu Val
             55                 60                 65

TCT AAC CCA GAC TTT AAG GTG GAA CAC GAT GGA TCT TTA GTT GCA CTG           296
Ser Asn Pro Asp Phe Lys Val Glu His Asp Gly Ser Leu Val Ala Leu
         70                 75                 80

AAG AAT GTA TCA GAA GCT GGC AGA GCT TTG TTT GTC CAT GCA CGG TCT           344
Lys Asn Val Ser Glu Ala Gly Arg Ala Leu Phe Val His Ala Arg Ser
 85              90                 95                  100

GAG CAT GCT GAG GAT ATG GCA GAA ATT TTG ATT GTT GGA GCT GAT GAG           392
Glu His Ala Glu Asp Met Ala Glu Ile Leu Ile Val Gly Ala Asp Glu
             105                110                115

AAG CAC GAT GCA TTA AAG GAA ATC TTT AAG ATA GAA GGC AAC CTT GGA           440
Lys His Asp Ala Leu Lys Glu Ile Phe Lys Ile Glu Gly Asn Leu Gly
             120                125                130

ATT CCA AGA CAA AAA AGG GCT ATT CTG GCG ACT CCA ATA TTA ATT CCA           488
Ile Pro Arg Gln Lys Arg Ala Ile Leu Ala Thr Pro Ile Leu Ile Pro
         135                140                145

GAA AAT CAA AGA CCA CCA TTT CCC AGA TCA GTT GGC AAG GTC ATC AGG           536
Glu Asn Gln Arg Pro Pro Phe Pro Arg Ser Val Gly Lys Val Ile Arg
     150                155                160

AGT GAA GGG ACA GAG GGA GCA AAG TTC CGA CTC TCT GGT AAG GGA GTA           584
Ser Glu Gly Thr Glu Gly Ala Lys Phe Arg Leu Ser Gly Lys Gly Val
165             170                175                180

GAT CAA GAC CCG AAA GGA ATT TTT AGA ATC AAT GAG ATC AGT GGG GAT           632
Asp Gln Asp Pro Lys Gly Ile Phe Arg Ile Asn Glu Ile Ser Gly Asp
             185                190                195

GTC TCT GTG ACC CGA CCC CTG GAT AGA GAA GCA ATA GCC AAT TAT GAG           680
Val Ser Val Thr Arg Pro Leu Asp Arg Glu Ala Ile Ala Asn Tyr Glu
             200                205                210

CTG GAA GTT GAA GTA ACG GAT TTA AGT GGG AAA ATC ATT GAT GGC CCA           728
Leu Glu Val Glu Val Thr Asp Leu Ser Gly Lys Ile Ile Asp Gly Pro
```

|  |  |  |  |  |  |  |  |  |  |  |  |  |  |  |  |
|---|---|---|---|---|---|---|---|---|---|---|---|---|---|---|---|
|  |  | 215 |  |  |  |  | 220 |  |  |  |  |  | 225 |  |  |
| GTC | CGC | TTA | GAT | ATT | TCT | GTT | ATT | GAT | CAA | AAT | GAT | AAC | AGG | CCG | ATG | 776
| Val | Arg | Leu | Asp | Ile | Ser | Val | Ile | Asp | Gln | Asn | Asp | Asn | Arg | Pro | Met |
|  | 230 |  |  |  | 235 |  |  |  |  | 240 |  |  |  |  |  |
| TTC | AAA | GAA | GGA | CCC | TAT | GTT | GGT | CAC | GTC | ATG | GAA | GGA | TCC | CCT | ACA | 824
| Phe | Lys | Glu | Gly | Pro | Tyr | Val | Gly | His | Val | Met | Glu | Gly | Ser | Pro | Thr |
| 245 |  |  |  |  | 250 |  |  |  |  | 255 |  |  |  |  | 260 |
| GGA | ACA | ACT | GTG | ATG | CGG | ATG | ACA | GCA | TTT | GAT | GCT | GAT | GAT | CCT | AGC | 872
| Gly | Thr | Thr | Val | Met | Arg | Met | Thr | Ala | Phe | Asp | Ala | Asp | Asp | Pro | Ser |
|  |  |  |  | 265 |  |  |  |  | 270 |  |  |  |  | 275 |  |
| ACA | GAC | AAC | GCT | CTT | CTG | CGG | TAT | AAC | ATC | CTC | AAG | CAG | ACA | CCT | ACC | 920
| Thr | Asp | Asn | Ala | Leu | Leu | Arg | Tyr | Asn | Ile | Leu | Lys | Gln | Thr | Pro | Thr |
|  |  |  | 280 |  |  |  |  | 285 |  |  |  |  | 290 |  |  |
| AAA | CCT | TCC | CCA | AAT | ATG | TTC | TAC | ATT | GAC | CCA | GAA | AAG | GGA | GAT | ATT | 968
| Lys | Pro | Ser | Pro | Asn | Met | Phe | Tyr | Ile | Asp | Pro | Glu | Lys | Gly | Asp | Ile |
|  |  | 295 |  |  |  |  | 300 |  |  |  |  | 305 |  |  |  |
| GTC | ACA | GTG | GTG | TCA | CCT | GTA | CTG | CTG | GAT | CGT | GAG | ACA | ATG | GAA | ACG | 1016
| Val | Thr | Val | Val | Ser | Pro | Val | Leu | Leu | Asp | Arg | Glu | Thr | Met | Glu | Thr |
|  | 310 |  |  |  |  | 315 |  |  |  |  | 320 |  |  |  |  |
| CCG | AAG | TAC | GAG | CTG | GTT | ATT | GAA | GCC | AAG | GAT | ATG | GGC | GGC | CAT | GAT | 1064
| Pro | Lys | Tyr | Glu | Leu | Val | Ile | Glu | Ala | Lys | Asp | Met | Gly | Gly | His | Asp |
| 325 |  |  |  |  | 330 |  |  |  |  | 335 |  |  |  |  | 340 |
| GTG | GGA | CTT | ACT | GGA | ACT | GCA | ACT | GCC | ACT | ATT | CTT | ATT | GAT | GAC | AAA | 1112
| Val | Gly | Leu | Thr | Gly | Thr | Ala | Thr | Ala | Thr | Ile | Leu | Ile | Asp | Asp | Lys |
|  |  |  |  | 345 |  |  |  |  | 350 |  |  |  |  | 355 |  |
| AAC | GAC | CAC | CCA | CCA | GAA | TTT | ACC | AAG | AAG | GAG | TTT | CAG | GCC | ACA | GTA | 1160
| Asn | Asp | His | Pro | Pro | Glu | Phe | Thr | Lys | Lys | Glu | Phe | Gln | Ala | Thr | Val |
|  |  |  | 360 |  |  |  |  | 365 |  |  |  |  | 370 |  |  |
| AAG | GAA | GGA | GTC | ACA | GGA | GTA | ATA | GTA | AAC | TTA | ACT | GTT | GGT | GAC | CGA | 1208
| Lys | Glu | Gly | Val | Thr | Gly | Val | Ile | Val | Asn | Leu | Thr | Val | Gly | Asp | Arg |
|  |  | 375 |  |  |  |  | 380 |  |  |  |  | 385 |  |  |  |
| GAT | GAC | CCA | GCA | ACT | GGA | GCA | TGG | AGA | GCT | GTC | TAC | ACT | ATT | ATT | AAC | 1256
| Asp | Asp | Pro | Ala | Thr | Gly | Ala | Trp | Arg | Ala | Val | Tyr | Thr | Ile | Ile | Asn |
|  | 390 |  |  |  |  | 395 |  |  |  |  | 400 |  |  |  |  |
| GGA | AAT | CCA | GGG | CAG | AGT | TTT | GAA | ATC | CAT | ACC | AAT | CCC | CAG | ACT | AAT | 1304
| Gly | Asn | Pro | Gly | Gln | Ser | Phe | Glu | Ile | His | Thr | Asn | Pro | Gln | Thr | Asn |
| 405 |  |  |  |  | 410 |  |  |  |  | 415 |  |  |  |  | 420 |
| GAG | GGA | ATG | CTC | TCT | GTT | GTC | AAA | CCT | TTA | GAC | TAT | GAG | ATT | TCA | GCA | 1352
| Glu | Gly | Met | Leu | Ser | Val | Val | Lys | Pro | Leu | Asp | Tyr | Glu | Ile | Ser | Ala |
|  |  |  |  | 425 |  |  |  |  | 430 |  |  |  |  | 435 |  |
| TTT | CAC | ACA | TTG | CTG | ATA | AAA | GTA | GAA | AAT | GAA | GAC | CCG | TTG | ATT | CCA | 1400
| Phe | His | Thr | Leu | Leu | Ile | Lys | Val | Glu | Asn | Glu | Asp | Pro | Leu | Ile | Pro |
|  |  |  | 440 |  |  |  |  | 445 |  |  |  |  | 450 |  |  |
| GAC | ATA | GCC | TAC | GGT | CCC | AGT | TCC | ACA | GCA | ACA | GTT | CAG | ATC | ACC | GTT | 1448
| Asp | Ile | Ala | Tyr | Gly | Pro | Ser | Ser | Thr | Ala | Thr | Val | Gln | Ile | Thr | Val |
|  |  | 455 |  |  |  |  | 460 |  |  |  |  | 465 |  |  |  |
| GAG | GAT | GTG | AAT | GAA | GGC | CCT | GTT | TTC | CAC | CCA | AAC | CCA | ATG | ACA | GTG | 1496
| Glu | Asp | Val | Asn | Glu | Gly | Pro | Val | Phe | His | Pro | Asn | Pro | Met | Thr | Val |
|  | 470 |  |  |  |  | 475 |  |  |  |  | 480 |  |  |  |  |
| ACA | AAA | CAA | GAG | AAC | ATC | CCT | ATT | GGC | AGC | ATT | GTG | TTA | ACA | GTA | AAT | 1544
| Thr | Lys | Gln | Glu | Asn | Ile | Pro | Ile | Gly | Ser | Ile | Val | Leu | Thr | Val | Asn |
| 485 |  |  |  |  | 490 |  |  |  |  | 495 |  |  |  |  | 500 |
| GCC | ACT | GAT | CCA | GAT | ACT | TTG | CAA | CAT | CAG | ACT | ATC | AGG | TAT | TCA | GTT | 1592
| Ala | Thr | Asp | Pro | Asp | Thr | Leu | Gln | His | Gln | Thr | Ile | Arg | Tyr | Ser | Val |
|  |  |  |  | 505 |  |  |  |  | 510 |  |  |  |  | 515 |  |
| TAC | AAG | GAT | CCA | GCA | AGC | TGG | CTA | GAG | ATT | AAT | CCC | ACC | AAT | GGT | ACC | 1640
| Tyr | Lys | Asp | Pro | Ala | Ser | Trp | Leu | Glu | Ile | Asn | Pro | Thr | Asn | Gly | Thr |
|  |  |  | 520 |  |  |  |  | 525 |  |  |  |  | 530 |  |  |
| GTT | GCC | ACC | ACT | GCT | GTC | CTG | GAT | CGG | GAA | TCT | CCT | CAT | GTT | CAG | GAT | 1688
| Val | Ala | Thr | Thr | Ala | Val | Leu | Asp | Arg | Glu | Ser | Pro | His | Val | Gln | Asp |

-continued

```
                535                          540                            545
AAC  AAA  TAC  ACT  GCT  CTC  TTC  CTG  GCA  ATA  GAC  AGT  GGT  AAC  CCT  CCT             1736
Asn  Lys  Tyr  Thr  Ala  Leu  Phe  Leu  Ala  Ile  Asp  Ser  Gly  Asn  Pro  Pro
     550                      555                      560

GCT  ACA  GGT  ACA  GGA  ACT  TTA  CAC  ATC  ACC  TTG  GAG  GAC  GTC  AAT  GAC             1784
Ala  Thr  Gly  Thr  Gly  Thr  Leu  His  Ile  Thr  Leu  Glu  Asp  Val  Asn  Asp
565       Gly            570                      575                          580

AAT  GTC  CCC  TCC  CTT  TAC  CCA  ACA  CTG  GCA  AAA  GTC  TGT  GAT  GAT  GCT             1832
Asn  Val  Pro  Ser  Leu  Tyr  Pro  Thr  Leu  Ala  Lys  Val  Cys  Asp  Asp  Ala
                    585                      590                          595

AAA  GAT  CTC  AGA  GTA  GTG  GTA  CTA  GGA  GCA  TCA  GAC  AAA  GAC  CTC  CAT             1880
Lys  Asp  Leu  Arg  Val  Val  Val  Leu  Gly  Ala  Ser  Asp  Lys  Asp  Leu  His
               600                      605                      610

CCC  AAC  ACA  GAT  CCA  TTT  AAA  TTT  GAA  CTG  AGT  AAG  CAA  TCT  GGT  CCA             1928
Pro  Asn  Thr  Asp  Pro  Phe  Lys  Phe  Glu  Leu  Ser  Lys  Gln  Ser  Gly  Pro
               615                      620                      625

GAA  AAG  TTA  TGG  AGA  ATC  AAC  AAG  CTT  AAC  AAT  ACT  CAT  GCC  CAG  GTT             1976
Glu  Lys  Leu  Trp  Arg  Ile  Asn  Lys  Leu  Asn  Asn  Thr  His  Ala  Gln  Val
     630                      635                      640

GTC  CTG  CTT  CAA  AAC  CTG  AAA  AAG  GCC  AAT  TAC  AAC  ATC  CCA  ATC  TCA             2024
Val  Leu  Leu  Gln  Asn  Leu  Lys  Lys  Ala  Asn  Tyr  Asn  Ile  Pro  Ile  Ser
645                      650                      655                          660

GTG  ACA  GAT  TCT  GGA  AAA  CCA  CCT  CTG  ACT  AAC  AAC  ACA  GAA  CTG  AAA             2072
Val  Thr  Asp  Ser  Gly  Lys  Pro  Pro  Leu  Thr  Asn  Asn  Thr  Glu  Leu  Lys
                    665                      670                          675

TTA  CAA  GTG  TGT  TCC  TGC  AAG  AAA  TCC  AGA  ATG  GAC  TGC  AGT  GCA  AGT             2120
Leu  Gln  Val  Cys  Ser  Cys  Lys  Lys  Ser  Arg  Met  Asp  Cys  Ser  Ala  Ser
               680                      685                      690

GAT  GCC  CTT  CAT  ATC  AGC  ATG  ACT  CTT  ATC  CTT  CTT  TCA  CTC  TTC  AGT             2168
Asp  Ala  Leu  His  Ile  Ser  Met  Thr  Leu  Ile  Leu  Leu  Ser  Leu  Phe  Ser
               695                      700                      705

TTA  TTT  TGT  CTG  T     AGGAACTCCT  GACATTTGAA  GCTGTCCTAC  CGAGTTGCCA                   2221
Leu  Phe  Cys  Leu
               710

TGGCAACGAG  AAAAAAGAAA  ACGTCAGATC  TGAAGACTGC  AGTTTACAGT  TACTGTTCTT                    2281

CACTACTAGG  CCTCAGTTGC  TCCAGATTCA  GTTTAATTTG  CAACCTCACT  TAATCTGTCC                    2341

GACTATACAT  TGGTGTTTGA  CAGCCTCTGC  CCTAACTTCC  ATTTATTAAT  GGATTCCTCT                    2401

TGCAAGATGC  AAGGTTTATG  CGAATTTTCA  CTGAATGTTA  AAAGACCATG  ACATCTAAAC                    2461

TTGACCTTTG  GGGAGCAGAA  AACAGATTGA  CTCCATTTTT  TTCTAACTGT  TGACTTGTTG                    2521

CTATTCAACT  GTTCAGAAAA  TATTTTGTCT  GTGGGTTAGT  ATTTGTATAT  GTATGAGTGT                    2581

ATGTATATAT  ATATATATTT  ATATGGAGAG  AAGAGTTATA  GGACTGGTTT  AGCTTTTATA                    2641

AAATATTCAT  CTGGAATGTG  CAAATGACAA  AGCAGAGTAA  TACAGCCACA  GATGAATCAT                    2701

AACTATTCAA  CATGGCTAAA  CCTACTGTAC  TTGCTGTTTA  TAGTGTGGCC  AGAAGGAGAG                    2761

CCTATTGCAG  TCATACCACT  GAAAAAGCC   ACTTTGTTGA  CACCAAATAA  GGCAGGCCCA                    2821

GGGCTCTGCA  GCATCACTTC  TTGTACCTCA  GGTTCAGCAA  ACAGGAAATG  CAAGTCCCCC                    2881

GGCTTGCTTC  TGATCCGGAC  TTCTCACCTT  ATGCCCCAAA  ACTGACTTTA  AGACTCAGCG                    2941

GGAGCACATC  TCTTCATCTC  AGTGCCGGGA  GGGTACGCAA  GCTCTCACCT  GTAAGGCAAG                    3001

GGGAAGCACT  CAGCACAGCC  AGCACCATAT  GGTCACCACC  TACAGCAATG  GGACCTGCTG                    3061

GGCTGATTTT  AAAGGGGCTA  AACTCAGCTT  CCTCTATGCT  CTTGCAGATA  ATTATTTGCT                    3121

GGGGCAGTTT  ACAAAATTTA  AGTCCTTTGT  CAGTTCTGCA  GACGAAGTAG  GTAATGTCTG                    3181

CTTATGAGAA  GCTGATTAGA  ACAGCAAAAT  CAAGGTGTTT  CCCAGAAGCA  CTGGCCTCTC                    3241
```

```
TCTCAGCCTC TGTGCAGCTG TCATTACATG TATCAGTGCA AGGAGGAAAA CAGATGCCCT    3301

ATTATCTAAG TGTATTCACA CATATCTATA GTTTGAATA TATATATACA TACATACACG     3361

TGTACACACA GTTTCCAGTT AAGAGTAACA AGAGCATTTC TTTGTGTGTG TAAACTTACC    3421

ACACTTGTTT GCAGACATGG GGAAAAAAAG GGTGTTCGTT ACATATGACT ATGAATCCTT    3481

TTTTATTCTG TGAGCATGTA AGGTTAAAA AAGAAAAAAC TTAACTGTAT CAAGATGATC     3541

ATCTTGTTAA TAAATTGTAA ATGATCCATC AAAGCTCACA CCAAATTTTT ATAAAATTAA    3601

CACAGAAAAG TATACTAGTG ACAGACTGTG GCTTTTATTA GAGCTTGCCA GTAACTAGGG    3661

TAAGGTAAGT GTCTTAGAAT ATTTTAATAA ACTTGCTTAT TTAAAGTTTA AACAAGAAAG    3721

CTTCCTTATG CAATAGTACT TTGCAGCTGC ATTCTTTAGT TAGCATTTTT ACAGTACCTA    3781

TGAGTCATAC TGTATGTTGT CTTTACTACA GTGAGATTAT GAGCATATCT TCCACACCAC    3841

ATATATGTTT CAATAGTAAA GTTTTTTGGA AGCATTAAAG AGTCCAAACA TACACTGAGT    3901

TTTCCATAAC GCTACACTAG ATATTAAATG TGTGTTGGTG GTTAAAAAAA AAAAAAA      3959
```

( 2 ) INFORMATION FOR SEQ ID NO:2:

( i ) SEQUENCE CHARACTERISTICS:
        ( A ) LENGTH: 712 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln His Lys Thr Gln Leu Thr Leu Ser Phe Leu Leu Ser Gln Val
 1               5                  10                  15

Leu Leu Leu Ala Cys Ala Glu Asp Leu Glu Cys Thr Pro Gly Phe Gln
                20                  25                  30

Gln Lys Val Phe Tyr Ile Glu Gln Pro Phe Glu Phe Thr Glu Asp Gln
            35                  40                  45

Pro Ile Leu Asn Leu Val Phe Asp Asp Cys Lys Gly Asn Asn Lys Leu
        50                  55                  60

Asn Phe Glu Val Ser Asn Pro Asp Phe Lys Val Glu His Asp Gly Ser
 65                  70                  75                  80

Leu Val Ala Leu Lys Asn Val Ser Glu Ala Gly Arg Ala Leu Phe Val
                85                  90                  95

His Ala Arg Ser Glu His Ala Glu Asp Met Ala Glu Ile Leu Ile Val
                100                 105                 110

Gly Ala Asp Glu Lys His Asp Ala Leu Lys Glu Ile Phe Lys Ile Glu
            115                 120                 125

Gly Asn Leu Gly Ile Pro Arg Gln Lys Arg Ala Ile Leu Ala Thr Pro
        130                 135                 140

Ile Leu Ile Pro Glu Asn Gln Arg Pro Pro Phe Pro Arg Ser Val Gly
145                 150                 155                 160

Lys Val Ile Arg Ser Glu Gly Thr Glu Gly Ala Lys Phe Arg Leu Ser
                165                 170                 175

Gly Lys Gly Val Asp Gln Asp Pro Lys Gly Ile Phe Arg Ile Asn Glu
            180                 185                 190

Ile Ser Gly Asp Val Ser Val Thr Arg Pro Leu Asp Arg Glu Ala Ile
        195                 200                 205

Ala Asn Tyr Glu Leu Glu Val Glu Val Thr Asp Leu Ser Gly Lys Ile
        210                 215                 220

Ile Asp Gly Pro Val Arg Leu Asp Ile Ser Val Ile Asp Gln Asn Asp
225                 230                 235                 240
```

Asn Arg Pro Met Phe Lys Glu Gly Pro Tyr Val Gly His Val Met Glu
                245                 250                 255

Gly Ser Pro Thr Gly Thr Thr Val Met Arg Met Thr Ala Phe Asp Ala
                260                 265                 270

Asp Asp Pro Ser Thr Asp Asn Ala Leu Leu Arg Tyr Asn Ile Leu Lys
                275                 280                 285

Gln Thr Pro Thr Lys Pro Ser Pro Asn Met Phe Tyr Ile Asp Pro Glu
                290                 295                 300

Lys Gly Asp Ile Val Thr Val Ser Pro Val Leu Leu Asp Arg Glu
305                 310                 315                 320

Thr Met Glu Thr Pro Lys Tyr Glu Leu Val Ile Glu Ala Lys Asp Met
                325                 330                 335

Gly Gly His Asp Val Gly Leu Thr Gly Thr Ala Thr Ala Thr Ile Leu
                340                 345                 350

Ile Asp Asp Lys Asn Asp His Pro Pro Glu Phe Thr Lys Lys Glu Phe
                355                 360                 365

Gln Ala Thr Val Lys Glu Gly Val Thr Gly Val Ile Val Asn Leu Thr
                370                 375                 380

Val Gly Asp Arg Asp Asp Pro Ala Thr Gly Ala Trp Arg Ala Val Tyr
385                 390                 395                 400

Thr Ile Ile Asn Gly Asn Pro Gly Gln Ser Phe Glu Ile His Thr Asn
                405                 410                 415

Pro Gln Thr Asn Glu Gly Met Leu Ser Val Val Lys Pro Leu Asp Tyr
                420                 425                 430

Glu Ile Ser Ala Phe His Thr Leu Leu Ile Lys Val Glu Asn Glu Asp
                435                 440                 445

Pro Leu Ile Pro Asp Ile Ala Tyr Gly Pro Ser Ser Thr Ala Thr Val
                450                 455                 460

Gln Ile Thr Val Glu Asp Val Asn Glu Gly Pro Val Phe His Pro Asn
465                 470                 475                 480

Pro Met Thr Val Thr Lys Gln Glu Asn Ile Pro Ile Gly Ser Ile Val
                485                 490                 495

Leu Thr Val Asn Ala Thr Asp Pro Asp Thr Leu Gln His Gln Thr Ile
                500                 505                 510

Arg Tyr Ser Val Tyr Lys Asp Pro Ala Ser Trp Leu Glu Ile Asn Pro
                515                 520                 525

Thr Asn Gly Thr Val Ala Thr Ala Val Leu Asp Arg Glu Ser Pro
                530                 535                 540

His Val Gln Asp Asn Lys Tyr Thr Ala Leu Phe Leu Ala Ile Asp Ser
545                 550                 555                 560

Gly Asn Pro Pro Ala Thr Gly Thr Gly Thr Leu His Ile Thr Leu Glu
                565                 570                 575

Asp Val Asn Asp Asn Val Pro Ser Leu Tyr Pro Thr Leu Ala Lys Val
                580                 585                 590

Cys Asp Asp Ala Lys Asp Leu Arg Val Val Val Leu Gly Ala Ser Asp
                595                 600                 605

Lys Asp Leu His Pro Asn Thr Asp Pro Phe Lys Phe Glu Leu Ser Lys
    610                 615                 620

Gln Ser Gly Pro Glu Lys Leu Trp Arg Ile Asn Lys Leu Asn Asn Thr
625                 630                 635                 640

His Ala Gln Val Val Leu Leu Gln Asn Leu Lys Lys Ala Asn Tyr Asn
                645                 650                 655

Ile Pro Ile Ser Val Thr Asp Ser Gly Lys Pro Pro Leu Thr Asn Asn

```
                             660                          665                           670
Thr  Glu  Leu  Lys  Leu  Gln  Val  Cys  Ser  Cys  Lys  Lys  Ser  Arg  Met  Asp
               675                      680                      685

Cys  Ser  Ala  Ser  Asp  Ala  Leu  His  Ile  Ser  Met  Thr  Leu  Ile  Leu  Leu
     690                      695                     700

Ser  Leu  Phe  Ser  Leu  Phe  Cys  Leu
705                      710
```

( 2 ) INFORMATION FOR SEQ ID NO:3:

( i ) SEQUENCE CHARACTERISTICS:
        ( A ) LENGTH: 2779 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 40..2191

( x i ) SEQUENCE DESCRIPTION: SEQ ID NO:3:

```
GAATTCCAAA  AAGCCTCTGG  TACGTTCTAG  TCTGGCAAA  ATG  CAG  CAC  AAA  ACT                  54
                                               Met  Gln  His  Lys  Thr
                                                1                    5

CAA  CTT  ACT  CTG  TCC  TTT  CTG  CTG  TCC  CAG  GTT  CTG  TTG  CTT  GCG  TGT         102
Gln  Leu  Thr  Leu  Ser  Phe  Leu  Leu  Ser  Gln  Val  Leu  Leu  Leu  Ala  Cys
               10                      15                           20

GCA  GAA  GAT  TTA  GAA  TGC  ACC  CCT  GGA  TTC  CAG  CAA  AAG  GTT  TTT  TAT         150
Ala  Glu  Asp  Leu  Glu  Cys  Thr  Pro  Gly  Phe  Gln  Gln  Lys  Val  Phe  Tyr
                    25                       30                      35

ATT  GAA  CAG  CCA  TTT  GAA  TTC  ACA  GAG  GAC  CAG  CCA  ATT  CTG  AAC  CTG         198
Ile  Glu  Gln  Pro  Phe  Glu  Phe  Thr  Glu  Asp  Gln  Pro  Ile  Leu  Asn  Leu
               40                      45                           50

GTG  TTT  GAT  GAC  TGC  AAG  GGG  AAT  AAC  AAA  TTG  AAC  TTC  GAA  GTT  TCT         246
Val  Phe  Asp  Asp  Cys  Lys  Gly  Asn  Asn  Lys  Leu  Asn  Phe  Glu  Val  Ser
     55                      60                           65

AAC  CCA  GAC  TTT  AAG  GTG  GAA  CAC  GAT  GGA  TCT  TTA  GTT  GCA  CTG  AAG         294
Asn  Pro  Asp  Phe  Lys  Val  Glu  His  Asp  Gly  Ser  Leu  Val  Ala  Leu  Lys
70                      75                       80                           85

AAT  GTA  TCA  GAA  GCT  GGC  AGA  GCT  TTG  TTT  GTC  CAT  GCA  CGG  TCT  GAG         342
Asn  Val  Ser  Glu  Ala  Gly  Arg  Ala  Leu  Phe  Val  His  Ala  Arg  Ser  Glu
                    90                       95                          100

CAT  GCT  GAG  GAT  ATG  GCA  GAA  ATT  TTG  ATT  GTT  GGA  GCT  GAT  GAG  AAG         390
His  Ala  Glu  Asp  Met  Ala  Glu  Ile  Leu  Ile  Val  Gly  Ala  Asp  Glu  Lys
               105                      110                          115

CAC  GAT  GCA  TTA  AAG  GAA  ATC  TTT  AAG  ATA  GAA  GGC  AAC  CTT  GGA  ATT         438
His  Asp  Ala  Leu  Lys  Glu  Ile  Phe  Lys  Ile  Glu  Gly  Asn  Leu  Gly  Ile
          120                      125                           130

CCA  AGA  CAA  AAA  AGG  GCT  ATT  CTG  GCG  ACT  CCA  ATA  TTA  ATT  CCA  GAA         486
Pro  Arg  Gln  Lys  Arg  Ala  Ile  Leu  Ala  Thr  Pro  Ile  Leu  Ile  Pro  Glu
135                      140                          145

AAT  CAA  AGA  CCA  CCA  TTT  CCC  AGA  TCA  GTT  GGC  AAG  GTC  ATC  AGG  AGT         534
Asn  Gln  Arg  Pro  Pro  Phe  Pro  Arg  Ser  Val  Gly  Lys  Val  Ile  Arg  Ser
150                      155                          160                     165

GAA  GGG  ACA  GAG  GGA  GCA  AAG  TTC  CGA  CTC  TCT  GGT  AAG  GGA  GTA  GAT         582
Glu  Gly  Thr  Glu  Gly  Ala  Lys  Phe  Arg  Leu  Ser  Gly  Lys  Gly  Val  Asp
                    170                      175                          180

CAA  GAC  CCG  AAA  GGA  ATT  TTT  AGA  ATC  AAT  GAG  ATC  AGT  GGG  GAT  GTC         630
Gln  Asp  Pro  Lys  Gly  Ile  Phe  Arg  Ile  Asn  Glu  Ile  Ser  Gly  Asp  Val
               185                      190                          195

TCT  GTG  ACC  CGA  CCC  CTG  GAT  AGA  GAA  GCA  ATA  GCC  AAT  TAT  GAG  CTG         678
Ser  Val  Thr  Arg  Pro  Leu  Asp  Arg  Glu  Ala  Ile  Ala  Asn  Tyr  Glu  Leu
```

```
                    200                          205                              210
GAA  GTT  GAA  GTA  ACG  GAT  TTA  AGT  GGG  AAA  ATC  ATT  GAT  GGC  CCA  GTC      726
Glu  Val  Glu  Val  Thr  Asp  Leu  Ser  Gly  Lys  Ile  Ile  Asp  Gly  Pro  Val
     215                      220                      225

CGC  CTA  GAT  ATT  TCT  GTT  ATT  GAT  CAA  AAT  GAT  AAC  AGG  CCG  ATG  TTC      774
Arg  Leu  Asp  Ile  Ser  Val  Ile  Asp  Gln  Asn  Asp  Asn  Arg  Pro  Met  Phe
230                      235                      240                      245

AAA  GAA  GGA  CCC  TAT  GTT  GGT  CAC  GTC  ATG  GAA  GGA  TCC  CCT  ACA  GGA      822
Lys  Glu  Gly  Pro  Tyr  Val  Gly  His  Val  Met  Glu  Gly  Ser  Pro  Thr  Gly
                         250                      255                      260

ACA  ACT  GTG  ATG  CGG  ATG  ACA  GCA  TTT  GAT  GCT  GAT  GAT  CCT  AGC  ACA      870
Thr  Thr  Val  Met  Arg  Met  Thr  Ala  Phe  Asp  Ala  Asp  Asp  Pro  Ser  Thr
               265                      270                      275

GAC  AAC  GCT  CTT  CTG  CGG  TAT  AAC  ATC  CTC  AAG  CAG  ACA  CCT  ACC  AAA      918
Asp  Asn  Ala  Leu  Leu  Arg  Tyr  Asn  Ile  Leu  Lys  Gln  Thr  Pro  Thr  Lys
          280                      285                      290

CCT  TCC  CCA  AAT  ATG  TTC  TAC  ATT  GAC  CCA  GAA  AAG  GGA  GAT  ATT  GTC      966
Pro  Ser  Pro  Asn  Met  Phe  Tyr  Ile  Asp  Pro  Glu  Lys  Gly  Asp  Ile  Val
     295                      300                      305

ACA  GTG  GTG  TCG  CCT  GTA  CTG  CTG  GAT  CGT  GAG  ACA  ATG  GAA  ACG  CCG     1014
Thr  Val  Val  Ser  Pro  Val  Leu  Leu  Asp  Arg  Glu  Thr  Met  Glu  Thr  Pro
310                      315                      320                      325

AAG  TAC  GAG  CTG  GTT  ATT  GAA  GCC  AAG  GAT  ATG  GGC  GGC  CAT  GAT  GTG     1062
Lys  Tyr  Glu  Leu  Val  Ile  Glu  Ala  Lys  Asp  Met  Gly  Gly  His  Asp  Val
                         330                      335                      340

GGA  CTT  ACT  GGA  ACT  GCA  ACT  GCC  ACT  ATT  CTT  ATT  GAT  GAC  AAA  AAC     1110
Gly  Leu  Thr  Gly  Thr  Ala  Thr  Ala  Thr  Ile  Leu  Ile  Asp  Asp  Lys  Asn
               345                      350                      355

GAC  CAC  CCA  CCA  GAA  TTT  ACC  AAG  AAG  GAG  TTT  CAG  GCC  ACA  GTA  AAG     1158
Asp  His  Pro  Pro  Glu  Phe  Thr  Lys  Lys  Glu  Phe  Gln  Ala  Thr  Val  Lys
          360                      365                      370

GAA  GGA  GTC  ACA  GGA  GTA  ATA  GTA  AAC  TTA  ACT  GTT  GGT  GAC  CGA  GAT     1206
Glu  Gly  Val  Thr  Gly  Val  Ile  Val  Asn  Leu  Thr  Val  Gly  Asp  Arg  Asp
     375                      380                      385

GAC  CCA  GCA  ACT  GGA  GCA  TGG  AGA  GCT  GTC  TAC  ACT  ATT  ATT  AAC  GGA     1254
Asp  Pro  Ala  Thr  Gly  Ala  Trp  Arg  Ala  Val  Tyr  Thr  Ile  Ile  Asn  Gly
390                      395                      400                      405

AAT  CCA  GGG  CAG  AGT  TTT  GAA  ATC  CAT  ACC  AAT  CCC  CAG  ACT  AAT  GAG     1302
Asn  Pro  Gly  Gln  Ser  Phe  Glu  Ile  His  Thr  Asn  Pro  Gln  Thr  Asn  Glu
                         410                      415                      420

GGA  ATG  CTC  TCT  GTT  GTC  AAA  CCT  TTA  GAT  TAT  GAG  ATT  TCA  GCA  TTT     1350
Gly  Met  Leu  Ser  Val  Val  Lys  Pro  Leu  Asp  Tyr  Glu  Ile  Ser  Ala  Phe
               425                      430                      435

CAC  ACA  TTG  CTG  ATA  AAA  GTA  GAA  AAT  GAA  GAC  CCG  TTG  ATT  CCA  GAC     1398
His  Thr  Leu  Leu  Ile  Lys  Val  Glu  Asn  Glu  Asp  Pro  Leu  Ile  Pro  Asp
          440                      445                      450

ATA  GCC  TAC  GGT  CCC  AGT  TCC  ACA  GCA  ACA  GTT  CAG  ATC  ACC  GTT  GAG     1446
Ile  Ala  Tyr  Gly  Pro  Ser  Ser  Thr  Ala  Thr  Val  Gln  Ile  Thr  Val  Glu
     455                      460                      465

GAT  GTG  AAT  GAA  GGC  CCT  GTT  TTC  CAC  CCA  AAC  CCA  ATG  ACA  GTG  ACA     1494
Asp  Val  Asn  Glu  Gly  Pro  Val  Phe  His  Pro  Asn  Pro  Met  Thr  Val  Thr
470                      475                      480                      485

AAA  CAA  GAG  AAC  ATC  CCT  ATT  GGC  AGC  ATT  GTG  TTA  ACA  GTA  AAT  GCC     1542
Lys  Gln  Glu  Asn  Ile  Pro  Ile  Gly  Ser  Ile  Val  Leu  Thr  Val  Asn  Ala
                         490                      495                      500

ACT  GAT  CCA  GAT  ACT  TTG  CAA  CAT  CAG  ACT  ATC  AGG  TAT  TCA  GTT  TAC     1590
Thr  Asp  Pro  Asp  Thr  Leu  Gln  His  Gln  Thr  Ile  Arg  Tyr  Ser  Val  Tyr
               505                      510                      515

AAG  GAT  CCA  GCA  AGC  TGG  CTA  GAG  ATT  AAT  CCC  ACC  AAT  GGT  ACC  GTT     1638
Lys  Asp  Pro  Ala  Ser  Trp  Leu  Glu  Ile  Asn  Pro  Thr  Asn  Gly  Thr  Val
```

-continued

```
                     520                        525                            530
GCC  ACC  ACT  GCT  GTC  CTG  GAT  CGG  GAA  TCT  CCG  CAT  GTT  CAG  GAT  AAC    1686
Ala  Thr  Thr  Ala  Val  Leu  Asp  Arg  Glu  Ser  Pro  His  Val  Gln  Asp  Asn
     535                      540                 545

AAA  TAC  ACT  GCT  CTC  TTC  CTG  GCA  ATA  GAC  AGT  GGT  AAC  CCT  CCT  GCT    1734
Lys  Tyr  Thr  Ala  Leu  Phe  Leu  Ala  Ile  Asp  Ser  Gly  Asn  Pro  Pro  Ala
550                           555                 560                      565

ACA  GGT  ACA  GGA  ACT  TTA  CAC  ATC  ACC  TTG  GAG  GAC  GTC  AAT  GAC  AAT    1782
Thr  Gly  Thr  Gly  Thr  Leu  His  Ile  Thr  Leu  Glu  Asp  Val  Asn  Asp  Asn
                    570                      575                           580

GTC  CCC  TCC  CTT  TAC  CCA  ACA  CTG  GCA  AAA  GTC  TGT  GAT  GAT  GCT  AAA    1830
Val  Pro  Ser  Leu  Tyr  Pro  Thr  Leu  Ala  Lys  Val  Cys  Asp  Asp  Ala  Lys
               585                      590                      595

GAT  CTC  AGA  GTA  GTG  GTT  CTA  GGA  GCA  TCA  GAC  AAA  GAC  CTC  CAT  CCC    1878
Asp  Leu  Arg  Val  Val  Val  Leu  Gly  Ala  Ser  Asp  Lys  Asp  Leu  His  Pro
          600                      605                      610

AAC  ACA  GAT  CCA  TTT  AAA  TTT  GAA  CTG  AGT  AAG  CAA  TCT  GGT  CCA  GAA    1926
Asn  Thr  Asp  Pro  Phe  Lys  Phe  Glu  Leu  Ser  Lys  Gln  Ser  Gly  Pro  Glu
     615                      620                 625

AAG  TTA  TGG  AGA  ATC  AAC  AAG  CTT  AAC  AAT  ACT  CAT  GCC  CAG  GTT  GTC    1974
Lys  Leu  Trp  Arg  Ile  Asn  Lys  Leu  Asn  Asn  Thr  His  Ala  Gln  Val  Val
630                           635                 640                      645

CTG  CTT  CAA  AAC  CTG  AAA  AAG  GCC  AAT  TAC  AAC  ATC  CCA  ATC  TCA  GTG    2022
Leu  Leu  Gln  Asn  Leu  Lys  Lys  Ala  Asn  Tyr  Asn  Ile  Pro  Ile  Ser  Val
                    650                      655                      660

ACA  GAT  TCT  GGA  AAA  CCA  CCT  CTG  ACT  AAC  AAC  ACA  GAA  CTG  AAA  TTA    2070
Thr  Asp  Ser  Gly  Lys  Pro  Pro  Leu  Thr  Asn  Asn  Thr  Glu  Leu  Lys  Leu
               665                      670                      675

CAA  GTG  TGT  TCC  TGC  AAG  AAA  TCC  AGA  ATG  GAC  TGC  AGT  GCA  AGT  GAT    2118
Gln  Val  Cys  Ser  Cys  Lys  Lys  Ser  Arg  Met  Asp  Cys  Ser  Ala  Ser  Asp
          680                      685                      690

GCC  CTT  CAT  ATC  AGC  ATG  ACT  CTT  ATC  CTT  CTT  TCA  CTC  TTC  AGT  TTA    2166
Ala  Leu  His  Ile  Ser  Met  Thr  Leu  Ile  Leu  Leu  Ser  Leu  Phe  Ser  Leu
     695                      700                 705

TTT  TGT  AAG  TCT  TTT  CCT  TAT  GTG  T AAGCATTGAA CGTTATTTAT                   2211
Phe  Cys  Lys  Ser  Phe  Pro  Tyr  Val
710                      715

CTGCTTGCTT  TTGCACTATA  AGAAACCTTA  CCAAGAGAGA  AGTTAACTTT  ATTTTTTCCC    2271

TGCGGTAGAT  GCTATACAGA  AGTAGGAGGG  GAGGGATTTT  TCACAGTCAA  AAAATAGCAA    2331

CAAATGCCGG  GTTGTCAAAT  TAAGAAATAG  AAGCAATAAT  TCTAGGAAGA  ATCAAAGAGA    2391

ATTAAAGCTA  GCATATGATA  AACTAAGAAG  TACCAGCTGT  AGTAACAGAT  TTCTGAGATG    2451

CTTTCTTTCA  TCTCTCCCCA  CTTGAATTCA  ATTCAAAAGC  AGAAACTGAA  GATTAAAAGG    2511

TGTTCTTGTA  ACAATAACTG  TTCTGGGTCA  CCATGAAAAT  GAGTACTGTC  TGCTTCAATC    2571

TATTTGTCCG  TAAAGTGCGC  GAGCAATTGG  AACATAAGGA  ACTTACTGAA  GATTCTGGGT    2631

TTAGAGACAC  TCAAACTGAT  AACCAGAATA  GCAGGTCTGT  GTTGAGGGAG  AGAGAACTGA    2691

TGCATAAAGG  AAGCTTCTGC  TGCTTTAGAG  AAAGCTTTCT  AAAAGTCTTA  TGAAATTCCT    2751

AATCTGAATT  AGGAGTTTAA  AGGAATTC                                          2779
```

( 2 ) INFORMATION FOR SEQ ID NO:4:

( i ) SEQUENCE CHARACTERISTICS:
        ( A ) LENGTH: 717 amino acids
        ( B ) TYPE: amino acid
        ( D ) TOPOLOGY: linear ( i i ) MOLECULE TYPE: protein (xi) SEQUENCE DESCRIPTION: SEQ ID NO:4:

| Met | Gln | His | Lys | Thr | Gln | Leu | Thr | Leu | Ser | Phe | Leu | Leu | Ser | Gln | Val |
|---|---|---|---|---|---|---|---|---|---|---|---|---|---|---|---|
| 1 | | | | 5 | | | | | 10 | | | | | 15 | |
| Leu | Leu | Leu | Ala | Cys | Ala | Glu | Asp | Leu | Glu | Cys | Thr | Pro | Gly | Phe | Gln |
| | | | 20 | | | | 25 | | | | | 30 | | | |
| Gln | Lys | Val | Phe | Tyr | Ile | Glu | Gln | Pro | Phe | Glu | Phe | Thr | Glu | Asp | Gln |
| | | 35 | | | | | 40 | | | | | 45 | | | |
| Pro | Ile | Leu | Asn | Leu | Val | Phe | Asp | Asp | Cys | Lys | Gly | Asn | Asn | Lys | Leu |
| | 50 | | | | | 55 | | | | | 60 | | | | |
| Asn | Phe | Glu | Val | Ser | Asn | Pro | Asp | Phe | Lys | Val | Glu | His | Asp | Gly | Ser |
| 65 | | | | | 70 | | | | | 75 | | | | | 80 |
| Leu | Val | Ala | Leu | Lys | Asn | Val | Ser | Glu | Ala | Gly | Arg | Ala | Leu | Phe | Val |
| | | | | 85 | | | | | 90 | | | | | 95 | |
| His | Ala | Arg | Ser | Glu | His | Ala | Glu | Asp | Met | Ala | Glu | Ile | Leu | Ile | Val |
| | | | 100 | | | | | 105 | | | | | 110 | | |
| Gly | Ala | Asp | Glu | Lys | His | Asp | Ala | Leu | Lys | Glu | Ile | Phe | Lys | Ile | Glu |
| | | | 115 | | | | 120 | | | | | 125 | | | |
| Gly | Asn | Leu | Gly | Ile | Pro | Arg | Gln | Lys | Arg | Ala | Ile | Leu | Ala | Thr | Pro |
| | | 130 | | | | | 135 | | | | | 140 | | | |
| Ile | Leu | Ile | Pro | Glu | Asn | Gln | Arg | Pro | Pro | Phe | Pro | Arg | Ser | Val | Gly |
| 145 | | | | | 150 | | | | | 155 | | | | | 160 |
| Lys | Val | Ile | Arg | Ser | Glu | Gly | Thr | Glu | Gly | Ala | Lys | Phe | Arg | Leu | Ser |
| | | | | 165 | | | | | 170 | | | | | 175 | |
| Gly | Lys | Gly | Val | Asp | Gln | Asp | Pro | Lys | Gly | Ile | Phe | Arg | Ile | Asn | Glu |
| | | | 180 | | | | | 185 | | | | | 190 | | |
| Ile | Ser | Gly | Asp | Val | Ser | Val | Thr | Arg | Pro | Leu | Asp | Arg | Glu | Ala | Ile |
| | | 195 | | | | | 200 | | | | | 205 | | | |
| Ala | Asn | Tyr | Glu | Leu | Glu | Val | Glu | Val | Thr | Asp | Leu | Ser | Gly | Lys | Ile |
| | 210 | | | | | 215 | | | | | 220 | | | | |
| Ile | Asp | Gly | Pro | Val | Arg | Leu | Asp | Ile | Ser | Val | Ile | Asp | Gln | Asn | Asp |
| 225 | | | | | 230 | | | | | 235 | | | | | 240 |
| Asn | Arg | Pro | Met | Phe | Lys | Glu | Gly | Pro | Tyr | Val | Gly | His | Val | Met | Glu |
| | | | | 245 | | | | | 250 | | | | | 255 | |
| Gly | Ser | Pro | Thr | Gly | Thr | Thr | Val | Met | Arg | Met | Thr | Ala | Phe | Asp | Ala |
| | | | 260 | | | | | 265 | | | | | 270 | | |
| Asp | Asp | Pro | Ser | Thr | Asp | Asn | Ala | Leu | Leu | Arg | Tyr | Asn | Ile | Leu | Lys |
| | | 275 | | | | | 280 | | | | | 285 | | | |
| Gln | Thr | Pro | Thr | Lys | Pro | Ser | Pro | Asn | Met | Phe | Tyr | Ile | Asp | Pro | Glu |
| | 290 | | | | | 295 | | | | | 300 | | | | |
| Lys | Gly | Asp | Ile | Val | Thr | Val | Val | Ser | Pro | Val | Leu | Leu | Asp | Arg | Glu |
| 305 | | | | | 310 | | | | | 315 | | | | | 320 |
| Thr | Met | Glu | Thr | Pro | Lys | Tyr | Glu | Leu | Val | Ile | Glu | Ala | Lys | Asp | Met |
| | | | | 325 | | | | | 330 | | | | | 335 | |
| Gly | Gly | His | Asp | Val | Gly | Leu | Thr | Gly | Thr | Ala | Thr | Ala | Thr | Ile | Leu |
| | | | 340 | | | | | 345 | | | | | 350 | | |
| Ile | Asp | Asp | Lys | Asn | Asp | His | Pro | Pro | Glu | Phe | Thr | Lys | Lys | Glu | Phe |
| | | 355 | | | | | 360 | | | | | 365 | | | |
| Gln | Ala | Thr | Val | Lys | Glu | Gly | Val | Thr | Gly | Val | Ile | Val | Asn | Leu | Thr |
| | 370 | | | | | 375 | | | | | 380 | | | | |
| Val | Gly | Asp | Arg | Asp | Asp | Pro | Ala | Thr | Gly | Ala | Trp | Arg | Ala | Val | Tyr |
| 385 | | | | | 390 | | | | | 395 | | | | | 400 |
| Thr | Ile | Ile | Asn | Gly | Asn | Pro | Gly | Gln | Ser | Phe | Glu | Ile | His | Thr | Asn |
| | | | | 405 | | | | | 410 | | | | | 415 | |

|     |     |     |     |     |     |     |     |     |     |     |     |     |     |
|-----|-----|-----|-----|-----|-----|-----|-----|-----|-----|-----|-----|-----|-----|
| Pro | Gln | Thr | Asn<br>420 | Glu | Gly | Met | Leu | Ser<br>425 | Val | Val | Lys | Pro<br>430 | Leu | Asp | Tyr |
| Glu | Ile | Ser<br>435 | Ala | Phe | His | Thr<br>440 | Leu | Leu | Ile | Lys | Val<br>445 | Glu | Asn | Glu | Asp |
| Pro | Leu<br>450 | Ile | Pro | Asp | Ile<br>455 | Ala | Tyr | Gly | Pro | Ser<br>460 | Ser | Thr | Ala | Thr | Val |
| Gln<br>465 | Ile | Thr | Val | Glu | Asp<br>470 | Val | Asn | Glu | Gly | Pro<br>475 | Val | Phe | His | Pro | Asn<br>480 |
| Pro | Met | Thr | Val | Thr<br>485 | Lys | Gln | Glu | Asn | Ile<br>490 | Pro | Ile | Gly | Ser | Ile<br>495 | Val |
| Leu | Thr | Val | Asn<br>500 | Ala | Thr | Asp | Pro<br>505 | Asp | Thr | Leu | Gln | His<br>510 | Gln | Thr | Ile |
| Arg | Tyr | Ser<br>515 | Val | Tyr | Lys | Asp | Pro<br>520 | Ala | Ser | Trp | Leu | Glu<br>525 | Ile | Asn | Pro |
| Thr | Asn<br>530 | Gly | Thr | Val | Ala | Thr<br>535 | Thr | Ala | Val | Leu | Asp<br>540 | Arg | Glu | Ser | Pro |
| His<br>545 | Val | Gln | Asp | Asn | Lys<br>550 | Tyr | Thr | Ala | Leu | Phe<br>555 | Leu | Ala | Ile | Asp | Ser<br>560 |
| Gly | Asn | Pro | Pro | Ala<br>565 | Thr | Gly | Thr | Gly | Thr<br>570 | Leu | His | Ile | Thr | Leu<br>575 | Glu |
| Asp | Val | Asn | Asp<br>580 | Asn | Val | Pro | Ser | Leu<br>585 | Tyr | Pro | Thr | Leu | Ala<br>590 | Lys | Val |
| Cys | Asp | Asp<br>595 | Ala | Lys | Asp | Leu | Arg<br>600 | Val | Val | Val | Leu | Gly<br>605 | Ala | Ser | Asp |
| Lys | Asp<br>610 | Leu | His | Pro | Asn | Thr<br>615 | Asp | Pro | Phe | Lys | Phe<br>620 | Glu | Leu | Ser | Lys |
| Gln<br>625 | Ser | Gly | Pro | Glu | Lys<br>630 | Leu | Trp | Arg | Ile | Asn<br>635 | Lys | Leu | Asn | Asn | Thr<br>640 |
| His | Ala | Gln | Val | Val<br>645 | Leu | Leu | Gln | Asn | Leu<br>650 | Lys | Lys | Ala | Asn | Tyr<br>655 | Asn |
| Ile | Pro | Ile | Ser<br>660 | Val | Thr | Asp | Ser | Gly<br>665 | Lys | Pro | Pro | Leu | Thr<br>670 | Asn | Asn |
| Thr | Glu | Leu<br>675 | Lys | Leu | Gln | Val | Cys<br>680 | Ser | Cys | Lys | Lys | Ser<br>685 | Arg | Met | Asp |
| Cys | Ser | Ala<br>690 | Ser | Asp | Ala | Leu | His<br>695 | Ile | Ser | Met | Thr<br>700 | Leu | Ile | Leu | Leu |
| Ser<br>705 | Leu | Phe | Ser | Leu | Phe<br>710 | Cys | Lys | Ser | Phe | Pro<br>715 | Tyr | Val |     |     |     |

( 2 ) INFORMATION FOR SEQ ID NO:5:

( i ) SEQUENCE CHARACTERISTICS:
    ( A ) LENGTH: 913 amino acids
    ( B ) TYPE: amino acid
    ( D ) TOPOLOGY: linear ( x i ) SEQUENCE DESCRIPTION: SEQ ID NO:5:

|     |     |     |     |     |     |     |     |     |     |     |     |     |     |     |
|-----|-----|-----|-----|-----|-----|-----|-----|-----|-----|-----|-----|-----|-----|-----|
| Met<br>1 | Cys | Arg | Ile | Ala<br>5 | Gly | Thr | Pro | Pro | Arg<br>10 | Ile | Leu | Pro | Pro | Leu<br>15 | Ala |
| Leu | Met | Leu | Leu<br>20 | Ala | Ala | Leu | Gln | Gln<br>25 | Ala | Pro | Ile | Lys | Ala<br>30 | Thr | Cys |
| Glu | Asp | Met<br>35 | Leu | Cys | Lys | Met | Gly<br>40 | Phe | Pro | Glu | Asp | Val<br>45 | His | Ser | Ala |
| Val | Val<br>50 | Ser | Arg | Ser | Val | His<br>55 | Gly | Gly | Gln | Pro | Leu<br>60 | Leu | Asn | Val | Arg |
| Phe | Gln | Ser | Cys | Asp | Glu | Asn | Arg | Lys | Ile | Tyr | Phe | Gly | Ser | Ser | Glu |

```
        65                      70                     75                     80
Pro  Glu  Asp  Phe  Arg  Val  Gly  Glu  Asp  Val  Val  Tyr  Ala  Glu  Arg
                    85                   90                   95
Ser  Phe  Gln  Leu  Ser  Ala  Glu  Pro  Thr  Glu  Phe  Val  Val  Ser  Ala  Arg
               100                 105                      110
Asp  Lys  Glu  Thr  Gln  Glu  Glu  Trp  Gln  Met  Lys  Val  Lys  Leu  Thr  Pro
          115                      120                      125
Glu  Pro  Ala  Phe  Thr  Gly  Ala  Ser  Glu  Lys  Asp  Gln  Lys  Lys  Ile  Glu
     130                      135                      140
Asp  Ile  Ile  Phe  Pro  Trp  Gln  Gln  Tyr  Lys  Asp  Ser  Ser  His  Leu  Lys
145                      150                      155                      160
Arg  Gln  Lys  Arg  Asp  Trp  Val  Ile  Pro  Pro  Ile  Asn  Leu  Pro  Glu  Asn
                    165                      170                      175
Ser  Arg  Gly  Pro  Phe  Pro  Gln  Glu  Leu  Val  Arg  Ile  Arg  Ser  Asp  Arg
               180                      185                      190
Asp  Lys  Ser  Leu  Ser  Leu  Arg  Tyr  Ser  Val  Thr  Gly  Pro  Gly  Ala  Asp
          195                      200                      205
Gln  Pro  Pro  Thr  Gly  Ile  Phe  Ile  Ile  Asn  Pro  Ile  Ser  Gly  Gln  Leu
     210                      215                      220
Ser  Val  Thr  Lys  Pro  Leu  Asp  Arg  Glu  Gln  Ile  Ala  Ser  Phe  His  Leu
225                      230                      235                      240
Arg  Ala  His  Ala  Val  Asp  Val  Asn  Gly  Asn  Gln  Val  Glu  Asn  Pro  Ile
                    245                      250                      255
Asp  Ile  Val  Ile  Asn  Val  Ile  Asp  Met  Asn  Asp  Asn  Arg  Pro  Glu  Phe
               260                      265                      270
Leu  His  Gln  Val  Trp  Asn  Gly  Thr  Val  Pro  Glu  Gly  Ser  Lys  Pro  Gly
          275                      280                      285
Thr  Tyr  Val  Met  Thr  Val  Thr  Ala  Ile  Asp  Ala  Asp  Asp  Pro  Asn  Ala
     290                      295                      300
Gln  Asn  Gly  Met  Leu  Arg  Tyr  Arg  Ile  Leu  Ser  Gln  Ala  Pro  Ser  Ser
305                      310                      315                      320
Pro  Ser  Pro  Asn  Met  Phe  Thr  Ile  Asn  Asn  Glu  Thr  Gly  Asp  Ile  Ile
                    325                      330                      335
Thr  Val  Ala  Ala  Gly  Leu  Asp  Arg  Glu  Lys  Val  Gln  Gln  Tyr  Thr  Leu
               340                      345                      350
Ile  Ile  Gln  Ala  Thr  Asp  Met  Glu  Gly  Asn  Pro  Thr  Tyr  Gly  Leu  Ser
          355                      360                      365
Asn  Thr  Ala  Thr  Ala  Val  Ile  Thr  Val  Thr  Asp  Val  Asn  Asp  Asn  Pro
     370                      375                      380
Pro  Glu  Phe  Thr  Ala  Met  Thr  Phe  Tyr  Gly  Glu  Val  Pro  Glu  Asn  Arg
385                      390                      395                      400
Val  Asp  Val  Ile  Val  Ala  Asn  Leu  Thr  Val  Thr  Asp  Lys  Asp  Gln  Pro
                    405                      410                      415
His  Thr  Pro  Ala  Trp  Asn  Ala  Arg  Tyr  Gln  Met  Thr  Gly  Gly  Asp  Pro
               420                      425                      430
Thr  Gly  Gln  Phe  Thr  Ile  Leu  Thr  Asp  Pro  Asn  Ser  Asn  Asp  Gly  Leu
          435                      440                      445
Val  Thr  Val  Val  Lys  Pro  Ile  Asp  Phe  Glu  Thr  Asn  Arg  Met  Phe  Val
     450                      455                      460
Leu  Thr  Val  Ala  Ala  Glu  Asn  Gln  Val  Pro  Leu  Ala  Lys  Gly  Ile  Gln
465                      470                      475                      480
His  Pro  Pro  Gln  Ser  Thr  Ala  Thr  Val  Ser  Ile  Thr  Val  Ile  Asp  Val
                    485                      490                      495
```

```
Asn Glu Ser Pro Tyr Phe Val Pro Asn Pro Lys Leu Val Arg Gln Glu
            500             505             510

Glu Gly Leu Leu Ala Gly Ser Met Leu Thr Thr Phe Thr Ala Arg Asp
        515             520             525

Pro Asp Arg Tyr Met Gln Thr Ser Leu Arg Tyr Ser Lys Leu Ser
    530             535             540

Asp Pro Ala Asn Trp Leu Lys Ile Asp Pro Val Asn Gly Gln Ile Thr
545             550             555             560

Thr Thr Ala Val Leu Asp Arg Glu Ser Ile Tyr Val Gln Asn Asn Met
            565             570             575

Tyr Asn Ala Thr Phe Leu Ala Ser Asp Asn Gly Ile Pro Pro Met Ser
        580             585             590

Gly Thr Gly Thr Leu Gln Ile Tyr Leu Leu Asp Ile Asn Asp Asn Ala
        595             600             605

Pro Gln Val Asn Pro Lys Glu Ala Thr Thr Cys Glu Thr Leu Gln Pro
    610             615             620

Asn Ala Ile Asn Ile Thr Ala Val Asp Pro Asp Ile Asp Pro Asn Ala
625             630             635             640

Gly Pro Phe Ala Phe Glu Leu Pro Asp Ser Pro Pro Ser Ile Lys Arg
            645             650             655

Asn Trp Thr Ile Val Arg Ile Ser Gly Asp His Ala Gln Leu Ser Leu
            660             665             670

Arg Ile Arg Phe Leu Glu Ala Gly Ile Tyr Asp Val Pro Ile Val Ile
        675             680             685

Thr Asp Ser Gly Asn Pro His Ala Ser Ser Thr Ser Val Leu Lys Val
    690             695             700

Lys Val Cys Gln Cys Asp Ile Asn Gly Asp Cys Thr Asp Val Asp Arg
705             710             715             720

Ile Val Gly Ala Gly Leu Gly Thr Gly Ala Ile Ile Ala Ile Leu Leu
            725             730             735

Cys Ile Ile Ile Leu Leu Ile Leu Val Leu Met Phe Val Val Trp Met
            740             745             750

Lys Arg Arg Asp Lys Glu Arg Gln Ala Lys Gln Leu Leu Ile Asp Pro
        755             760             765

Glu Asp Asp Val Arg Asp Asn Ile Leu Lys Tyr Asp Glu Glu Gly Gly
    770             775             780

Gly Glu Glu Asp Gln Asp Tyr Asp Leu Ser Gln Leu Gln Gln Pro Asp
785             790             795             800

Thr Val Glu Pro Asp Ala Ile Lys Pro Val Gly Ile Arg Arg Leu Asp
            805             810             815

Glu Arg Pro Ile His Ala Glu Pro Gln Tyr Pro Val Arg Ser Ala Ala
            820             825             830

Pro His Pro Gly Asp Ile Gly Asp Phe Ile Asn Glu Gly Leu Ala Lys
        835             840             845

Ala Ala Asp Asn Asp Pro Thr Ala Pro Pro Tyr Asp Ser Leu Leu Val
    850             855             860

Phe Asp Tyr Glu Gly Ser Gly Ser Thr Ala Gly Ser Leu Ser Ser Leu
865             870             875             880

Asn Ser Ser Ser Ser Gly Gly Glu Gln Asp Tyr Asp Tyr Leu Asn Asp
            885             890             895

Trp Gly Pro Arg Phe Lys Lys Leu Ala Asp Met Tyr Gly Gly Gly Asp
            900             905             910

Asp
```

( 2 ) INFORMATION FOR SEQ ID NO:6:

( i ) SEQUENCE CHARACTERISTICS:
        ( A ) LENGTH: 837 amino acids
        ( B ) TYPE: amino acid
        ( D ) TOPOLOGY: linear ( x i ) SEQUENCE DESCRIPTION: SEQ ID NO:6:

```
Asp Ser Val Ala Ala Gly Arg Glu Leu Gly Arg Val Ser Phe Ala Ala
 1               5                  10                  15

Cys Ser Gly Arg Pro Trp Ala Val Tyr Val Pro Thr Asp Thr Arg Phe
             20                  25                  30

Lys Val Asn Gly Asp Gly Val Val Ser Thr Lys Arg Pro Leu Thr Leu
         35                  40                  45

Tyr Gly Arg Lys Ile Ser Phe Thr Ile Tyr Ala Gln Asp Ala Met Gly
     50                  55                  60

Lys Arg His Ser Ala Arg Val Thr Val Gly Arg His Arg His Arg Arg
 65                  70                  75                  80

His His His Asn His His Leu Gln Asp Thr Thr Pro Ala Val Leu Thr
                 85                  90                  95

Phe Pro Lys His Asp Pro Gly Phe Leu Arg Arg Gln Lys Arg Asp Trp
            100                 105                 110

Val Ile Pro Pro Ile Ser Cys Leu Glu Asn His Arg Gly Pro Tyr Pro
            115                 120                 125

Met Arg Leu Val Gln Ile Lys Ser Asn Lys Asp Lys Glu Ser Lys Val
        130                 135                 140

Tyr Tyr Ser Ile Thr Gly Gln Gly Ala Asp Ser Pro Pro Val Gly Ile
145                 150                 155                 160

Phe Ile Ile Glu Arg Glu Thr Gly Trp Leu Glu Val Thr Glu Gln Leu
                165                 170                 175

Asp Arg Glu Lys Ile Asp Arg Tyr Thr Leu Leu Ser His Ala Val Ser
                180                 185                 190

Ala Ser Gly Gln Pro Val Glu Asp Pro Met Glu Ile Ile Ile Thr Val
        195                 200                 205

Met Asp Gln Asn Asp Asn Lys Pro Val Phe Ile Lys Glu Val Phe Val
210                 215                 220

Gly Tyr Ile Glu Glu Asn Ala Lys Pro Gly Thr Ser Val Met Thr Val
225                 230                 235                 240

Asn Ala Thr Asp Ala Asp Asp Ala Val Asn Thr Asp Asn Gly Ile Val
                245                 250                 255

Ser Tyr Ser Ile Val Ser Gln Gln Pro Pro Arg Pro His Pro Gln Met
                260                 265                 270

Phe Thr Ile Asp Pro Ala Lys Gly Ile Ile Ser Val Leu Gly Thr Gly
            275                 280                 285

Leu Asp Arg Glu Thr Thr Pro Asn Tyr Thr Leu Ile Val Gln Ala Thr
        290                 295                 300

Asp Gln Glu Gly Lys Gly Leu Ser Asn Thr Ala Thr Ala Ile Ile Glu
305                 310                 315                 320

Val Thr Asp Ala Asn Asp Asn Ile Pro Ile Phe Asn Pro Thr Met Tyr
                325                 330                 335

Glu Gly Val Val Glu Glu Asn Lys Pro Gly Thr Glu Val Ala Arg Leu
            340                 345                 350

Thr Val Thr Asp Gln Asp Ala Pro Gly Ser Pro Ala Trp Gln Ala Val
        355                 360                 365

Tyr His Ile Lys Ser Gly Asn Leu Asp Gly Ala Phe Ser Ile Ile Thr
```

-continued

```
                370                            375                            380
Asp  Pro  Ser  Thr  Asn  Asn  Gly  Ile  Leu  Lys  Thr  Ala  Lys  Gly  Leu  Asp
385                      390                      395                      400

Tyr  Glu  Thr  Lys  Ser  Arg  Tyr  Asp  Leu  Val  Val  Thr  Val  Glu  Asn  Lys
                    405                      410                      415

Val  Pro  Leu  Ser  Val  Pro  Ile  Thr  Leu  Ser  Thr  Ala  Ser  Val  Leu  Val
               420                      425                      430

Thr  Val  Leu  Asp  Val  Asn  Glu  Pro  Pro  Val  Phe  Val  Pro  Pro  Ile  Lys
          435                      440                      445

Arg  Val  Gly  Val  Pro  Glu  Asp  Leu  Pro  Val  Gly  Gln  Gln  Val  Thr  Ser
     450                      455                      460

Tyr  Thr  Ala  Glu  Asp  Pro  Asp  Arg  Asp  Met  Arg  Gln  Lys  Ile  Thr  Tyr
465                      470                      475                      480

Arg  Met  Gly  Ser  Asp  Pro  Ala  Gly  Trp  Leu  Tyr  Ile  His  Pro  Glu  Asn
                    485                      490                      495

Gly  Ile  Val  Thr  Ala  Thr  Gln  Pro  Leu  Asp  Arg  Glu  Ser  Val  His  Ala
               500                      505                      510

Ile  Asn  Ser  Thr  Tyr  Lys  Ala  Ile  Ile  Leu  Ala  Val  Asp  Asn  Gly  Ile
          515                      520                      525

Pro  Asp  Thr  Thr  Gly  Thr  Gly  Thr  Leu  Leu  Leu  Leu  Leu  Gln  Asp  Val
     530                      535                      540

Asn  Asp  Asn  Gly  Pro  Thr  Pro  Glu  Pro  Arg  Ser  Phe  Glu  Ile  Cys  Ser
545                      550                      555                      560

Arg  Gln  Pro  Glu  Lys  Gln  Ile  Leu  Ser  Ile  Val  Asp  Lys  Asp  Leu  Pro
                    565                      570                      575

Pro  His  Thr  Tyr  Pro  Phe  Lys  Ala  Ala  Leu  Glu  His  Gly  Ser  Ser  Asn
               580                      585                      590

Asn  Trp  Thr  Val  Glu  Ile  Arg  Gly  Gln  Asp  Glu  Leu  Ala  Met  Gly  Leu
          595                      600                      605

Lys  Lys  Glu  Leu  Glu  Pro  Gly  Glu  Tyr  Asn  Ile  Phe  Val  Lys  Leu  Thr
     610                      615                      620

Asp  Ser  Gln  Gly  Lys  Ala  Gln  Val  Thr  Gln  Val  Lys  Ala  Gln  Val  Cys
625                      630                      635                      640

Glu  Cys  Glu  Gly  Thr  Ala  Lys  Asn  Cys  Glu  Arg  Arg  Ser  Tyr  Ile  Val
                    645                      650                      655

Gly  Gly  Leu  Gly  Val  Pro  Ala  Ile  Leu  Gly  Ile  Leu  Gly  Gly  Ile  Leu
               660                      665                      670

Ala  Leu  Leu  Ile  Leu  Leu  Leu  Leu  Leu  Leu  Leu  Phe  Ala  Arg  Arg  Arg
          675                      680                      685

Lys  Val  Glu  Lys  Glu  Pro  Leu  Leu  Pro  Pro  Glu  Asp  Asp  Met  Arg  Asp
     690                      695                      700

Asn  Val  Tyr  Asn  Tyr  Asp  Glu  Glu  Gly  Gly  Gly  Glu  Glu  Asp  Gln  Asp
705                      710                      715                      720

Tyr  Asp  Leu  Ser  Gln  Leu  His  Arg  Gly  Leu  Asp  Ala  Arg  Pro  Glu  Val
                    725                      730                      735

Ile  Arg  Asn  Asp  Val  Ala  Pro  Pro  Leu  Met  Ala  Ala  Pro  Gln  Tyr  Arg
               740                      745                      750

Pro  Arg  Pro  Ala  Asn  Pro  Asp  Glu  Ile  Gly  Asn  Phe  Ile  Asp  Glu  Asn
          755                      760                      765

Leu  Lys  Ala  Ala  Asp  Thr  Asp  Pro  Thr  Ala  Pro  Pro  Tyr  Asp  Ser  Leu
     770                      775                      780

Leu  Val  Phe  Asp  Tyr  Glu  Gly  Gly  Gly  Ser  Glu  Ala  Thr  Ser  Leu  Ser
785                      790                      795                      800
```

-continued

```
Ser  Leu  Asn  Ser  Ser  Ala  Ser  Asp  Gln  Asp  Gln  Asp  Tyr  Asp  Tyr  Leu
               805                     810                     815

Asn  Glu  Trp  Gly  Asn  Arg  Phe  Lys  Lys  Leu  Ala  Glu  Leu  Tyr  Gly  Gly
               820                     825                     830

Gly  Glu  Asp  Asp  Glu
               835
```

( 2 ) INFORMATION FOR SEQ ID NO:7:

( i ) SEQUENCE CHARACTERISTICS:
       ( A ) LENGTH: 884 amino acids
       ( B ) TYPE: amino acid
       ( D ) TOPOLOGY: linear ( x i ) SEQUENCE DESCRIPTION: SEQ ID NO:7:

```
Met  Gly  Ala  Arg  Cys  Arg  Ser  Phe  Ser  Ala  Leu  Leu  Leu  Leu  Leu  Gln
1                    5                     10                      15

Val  Ser  Ser  Trp  Leu  Cys  Gln  Glu  Leu  Glu  Pro  Glu  Ser  Cys  Ser  Pro
               20                     25                      30

Gly  Phe  Ser  Ser  Glu  Val  Tyr  Thr  Phe  Pro  Val  Pro  Glu  Arg  His  Leu
               35                     40                      45

Glu  Arg  Gly  His  Val  Leu  Gly  Arg  Val  Arg  Phe  Glu  Gly  Cys  Thr  Gly
          50                     55                     60

Arg  Pro  Arg  Thr  Ala  Phe  Phe  Ser  Glu  Asp  Ser  Arg  Phe  Lys  Val  Ala
65                        70                     75                         80

Thr  Asp  Gly  Thr  Ile  Thr  Val  Lys  Arg  His  Leu  Lys  Leu  His  Lys  Leu
                    85                     90                      95

Glu  Thr  Ser  Phe  Leu  Val  Arg  Ala  Arg  Asp  Ser  Ser  His  Arg  Glu  Leu
               100                    105                     110

Ser  Thr  Lys  Val  Thr  Leu  Lys  Ser  Met  Gly  His  His  His  Arg  His
               115                    120                     125

His  His  Arg  Asp  Pro  Ala  Ser  Glu  Ser  Asn  Pro  Glu  Leu  Leu  Met  Phe
          130                    135                     140

Pro  Ser  Val  Tyr  Pro  Gly  Leu  Arg  Arg  Gln  Lys  Arg  Asp  Trp  Val  Ile
145                        150                    155                        160

Pro  Pro  Ile  Ser  Cys  Pro  Glu  Asn  Glu  Lys  Gly  Glu  Phe  Pro  Lys  Asn
               165                    170                     175

Leu  Val  Gln  Ile  Lys  Ser  Asn  Arg  Asp  Lys  Glu  Thr  Lys  Val  Phe  Tyr
               180                    185                     190

Ser  Ile  Thr  Gly  Gln  Gly  Ala  Asp  Lys  Pro  Pro  Val  Gly  Val  Phe  Ile
               195                    200                     205

Ile  Glu  Arg  Glu  Thr  Gly  Trp  Leu  Lys  Val  Thr  Gln  Pro  Leu  Asp  Arg
          210                    215                     220

Glu  Ala  Ile  Ala  Lys  Tyr  Ile  Leu  Tyr  Ser  His  Ala  Val  Ser  Ser  Asn
225                        230                    235                        240

Gly  Glu  Ala  Val  Glu  Asp  Pro  Met  Glu  Ile  Val  Ile  Thr  Val  Thr  Asp
                    245                    250                     255

Gln  Asn  Asp  Asn  Arg  Pro  Glu  Phe  Thr  Gln  Glu  Val  Phe  Glu  Gly  Ser
               260                    265                     270

Val  Ala  Glu  Gly  Ala  Val  Pro  Gly  Thr  Ser  Val  Met  Lys  Val  Ser  Ala
               275                    280                     285

Thr  Asp  Ala  Asp  Asp  Asp  Val  Asn  Thr  Tyr  Asn  Ala  Ala  Ile  Ala  Tyr
          290                    295                     300

Thr  Ile  Val  Ser  Gln  Asp  Pro  Glu  Leu  Pro  His  Lys  Asn  Met  Phe  Thr
305                        310                    315                        320

Val  Asn  Arg  Asp  Thr  Gly  Val  Ile  Ser  Val  Leu  Thr  Ser  Gly  Leu  Asp
```

```
                                    325                              330                              335
    Arg   Glu   Ser   Tyr   Pro   Thr   Tyr   Thr   Leu   Val   Val   Gln   Ala   Ala   Asp   Leu
                            340                              345                              350
    Gln   Gly   Glu   Gly   Leu   Ser   Thr   Thr   Ala   Lys   Ala   Val   Ile   Thr   Val   Lys
                355                              360                              365
    Asp   Ile   Asn   Asp   Asn   Ala   Pro   Val   Phe   Asn   Pro   Ser   Thr   Tyr   Gln   Gly
                370                              375                              380
    Gln   Val   Pro   Glu   Asn   Glu   Val   Asn   Ala   Arg   Ile   Ala   Thr   Leu   Lys   Val
    385                              390                              395                              400
    Thr   Asp   Asp   Asp   Ala   Pro   Asn   Thr   Pro   Ala   Trp   Lys   Val   Val   Tyr   Thr
                                  405                              410                              415
    Val   Val   Asn   Asp   Pro   Asp   Gln   Gln   Phe   Val   Val   Val   Thr   Asp   Pro   Thr
                            420                              425                              430
    Thr   Asn   Asp   Gly   Ile   Leu   Lys   Thr   Ala   Lys   Gly   Leu   Asp   Phe   Glu   Ala
                            435                              440                              445
    Lys   Gln   Gln   Tyr   Ile   Leu   His   Val   Arg   Val   Glu   Asn   Glu   Glu   Pro   Phe
                      450                              455                              460
    Glu   Gly   Ser   Leu   Val   Pro   Ser   Thr   Ala   Thr   Val   Thr   Val   Asp   Val   Val
    465                              470                              475                              480
    Asp   Val   Asn   Glu   Ala   Pro   Ile   Phe   Met   Pro   Ala   Glu   Arg   Arg   Val   Glu
                                  485                              490                              495
    Val   Pro   Glu   Asp   Phe   Gly   Val   Gly   Gln   Glu   Ile   Thr   Ser   Tyr   Thr   Ala
                            500                              505                              510
    Arg   Glu   Pro   Asp   Thr   Phe   Met   Asp   Gln   Lys   Ile   Thr   Tyr   Arg   Ile   Trp
                      515                              520                              525
    Arg   Asp   Thr   Ala   Asn   Trp   Leu   Glu   Ile   Asn   Pro   Glu   Thr   Gly   Ala   Ile
                      530                              535                              540
    Phe   Thr   Arg   Ala   Glu   Met   Asp   Arg   Glu   Asp   Ala   Glu   His   Val   Lys   Asn
    545                                    550                              555                        560
    Ser   Thr   Tyr   Val   Ala   Leu   Ile   Ile   Ala   Thr   Asp   Asp   Gly   Ser   Pro   Ile
                                  565                              570                              575
    Ala   Thr   Gly   Thr   Gly   Thr   Leu   Leu   Leu   Val   Leu   Leu   Asp   Val   Asn   Asp
                            580                              585                              590
    Asn   Ala   Pro   Ile   Pro   Glu   Pro   Arg   Asn   Met   Gln   Phe   Cys   Gln   Arg   Asn
                      595                              600                              605
    Pro   Gln   Pro   His   Ile   Ile   Thr   Ile   Leu   Asp   Pro   Asp   Leu   Pro   Pro   Asn
          610                              615                              620
    Thr   Ser   Pro   Phe   Thr   Ala   Glu   Leu   Thr   His   Gly   Ala   Ser   Val   Asn   Trp
    625                              630                              635                              640
    Thr   Ile   Glu   Tyr   Asn   Asp   Ala   Ala   Gln   Glu   Ser   Leu   Ile   Leu   Gln   Pro
                            645                              650                              655
    Arg   Lys   Asp   Leu   Glu   Ile   Gly   Glu   Tyr   Lys   Ile   His   Leu   Lys   Leu   Ala
                      660                              665                              670
    Asp   Asn   Gln   Asn   Lys   Asp   Gln   Val   Thr   Thr   Leu   Asp   Val   His   Val   Cys
                      675                              680                              685
    Asp   Cys   Glu   Gly   Thr   Val   Asn   Asn   Cys   Met   Lys   Ala   Gly   Ile   Val   Ala
          690                              695                              700
    Ala   Gly   Leu   Gln   Val   Pro   Ala   Ile   Leu   Gly   Ile   Leu   Gly   Gly   Ile   Leu
    705                              710                              715                              720
    Ala   Leu   Leu   Ile   Leu   Ile   Leu   Leu   Leu   Leu   Leu   Phe   Leu   Arg   Arg   Arg
                            725                              730                              735
    Thr   Val   Val   Lys   Glu   Pro   Leu   Leu   Pro   Pro   Asp   Asp   Asp   Thr   Arg   Asp
                      740                              745                              750
```

| | | | | | | | | | | | | | | |
|---|---|---|---|---|---|---|---|---|---|---|---|---|---|---|
| Asn | Val | Tyr | Tyr | Tyr | Asp | Glu | Glu | Gly | Gly | Gly | Glu | Glu | Asp | Gln | Asp |
|  | 755 |  |  |  | 760 |  |  |  |  | 765 |  |  |  |  |
| Phe | Asp | Leu | Ser | Gln | Leu | His | Arg | Gly | Leu | Asp | Ala | Arg | Pro | Glu | Val |
|  | 770 |  |  |  | 775 |  |  |  | 780 |  |  |  |  |  |
| Thr | Arg | Asn | Asp | Val | Ala | Pro | Thr | Leu | Met | Ser | Val | Pro | Gln | Tyr | Arg |
| 785 |  |  |  | 790 |  |  |  |  | 795 |  |  |  |  | 800 |
| Pro | Arg | Pro | Ala | Asn | Pro | Asp | Glu | Ile | Gly | Asn | Phe | Ile | Asp | Glu | Asn |
|  |  |  |  | 805 |  |  |  |  | 810 |  |  |  |  | 815 |
| Leu | Lys | Ala | Ala | Asp | Ser | Asp | Pro | Thr | Ala | Pro | Pro | Tyr | Asp | Ser | Leu |
|  |  |  | 820 |  |  |  | 825 |  |  |  |  | 830 |  |  |
| Leu | Val | Phe | Asp | Tyr | Glu | Gly | Ser | Gly | Ser | Glu | Ala | Ala | Ser | Leu | Ser |
|  |  | 835 |  |  |  | 840 |  |  |  |  | 845 |  |  |  |
| Ser | Leu | Asn | Ser | Ser | Glu | Ser | Asp | Gln | Asp | Gln | Asp | Tyr | Asp | Tyr | Leu |
|  | 850 |  |  |  | 855 |  |  |  |  | 860 |  |  |  |  |
| Asn | Glu | Trp | Gly | Asn | Arg | Phe | Lys | Lys | Leu | Ala | Asp | Met | Tyr | Gly | Gly |
| 865 |  |  |  |  | 870 |  |  |  |  | 875 |  |  |  |  | 880 |
| Gly | Glu | Asp | Asp |  |  |  |  |  |  |  |  |  |  |  |  |

( 2 ) INFORMATION FOR SEQ ID NO:8:

( i ) SEQUENCE CHARACTERISTICS:
( A ) LENGTH: 822 amino acids
( B ) TYPE: amino acid
( D ) TOPOLOGY: linear ( x i ) SEQUENCE DESCRIPTION: SEQ ID NO:8:

| | | | | | | | | | | | | | | |
|---|---|---|---|---|---|---|---|---|---|---|---|---|---|---|
| Met | Glu | Leu | Leu | Ser | Gly | Pro | His | Ala | Phe | Leu | Leu | Leu | Leu | Gln |
| 1 |  |  |  | 5 |  |  |  |  | 10 |  |  |  |  | 15 |
| Val | Cys | Trp | Leu | Arg | Ser | Val | Val | Ser | Glu | Pro | Tyr | Arg | Ala | Gly | Phe |
|  |  |  | 20 |  |  |  |  | 25 |  |  |  |  | 30 |  |
| Ile | Gly | Glu | Ala | Gly | Val | Thr | Leu | Glu | Val | Glu | Gly | Thr | Asp | Leu | Glu |
|  |  | 35 |  |  |  |  | 40 |  |  |  |  | 45 |  |  |
| Pro | Ser | Gln | Val | Leu | Gly | Lys | Val | Ala | Leu | Ala | Gly | Gln | Gly | Met | His |
|  | 50 |  |  |  |  | 55 |  |  |  |  | 60 |  |  |  |
| His | Ala | Asp | Asn | Gly | Asp | Ile | Ile | Met | Leu | Thr | Arg | Gly | Thr | Val | Gln |
| 65 |  |  |  |  | 70 |  |  |  |  | 75 |  |  |  |  | 80 |
| Gly | Gly | Lys | Asp | Ala | Met | His | Ser | Pro | Pro | Thr | Arg | Ile | Leu | Arg | Arg |
|  |  |  |  | 85 |  |  |  |  | 90 |  |  |  |  | 95 |  |
| Arg | Lys | Arg | Glu | Trp | Val | Met | Pro | Pro | Ile | Phe | Val | Pro | Glu | Asn | Gly |
|  |  |  | 100 |  |  |  |  | 105 |  |  |  |  | 110 |  |
| Lys | Gly | Pro | Phe | Pro | Gln | Arg | Leu | Asn | Gln | Leu | Lys | Ser | Asn | Lys | Asp |
|  |  |  | 115 |  |  |  |  | 120 |  |  |  |  | 125 |  |
| Arg | Gly | Thr | Lys | Ile | Phe | Tyr | Ser | Ile | Thr | Gly | Pro | Gly | Ala | Asp | Ser |
|  |  | 130 |  |  |  |  | 135 |  |  |  |  | 140 |  |  |
| Pro | Pro | Glu | Gly | Val | Phe | Thr | Ile | Glu | Lys | Glu | Ser | Gly | Trp | Leu | Leu |
| 145 |  |  |  |  | 150 |  |  |  |  | 155 |  |  |  |  | 160 |
| Leu | His | Met | Pro | Leu | Asp | Arg | Glu | Lys | Ile | Val | Lys | Tyr | Glu | Leu | Tyr |
|  |  |  |  | 165 |  |  |  |  | 170 |  |  |  |  | 175 |  |
| Gly | His | Ala | Val | Ser | Glu | Asn | Gly | Ala | Ser | Val | Glu | Glu | Pro | Met | Asn |
|  |  |  | 180 |  |  |  |  | 185 |  |  |  |  | 190 |  |
| Ile | Ser | Ile | Ile | Val | Thr | Asp | Gln | Asn | Asp | Asn | Lys | Pro | Lys | Phe | Thr |
|  |  | 195 |  |  |  |  | 200 |  |  |  |  | 205 |  |  |
| Gln | Asp | Thr | Phe | Arg | Gly | Ser | Val | Ile | Glu | Gly | Val | Met | Pro | Gly | Thr |
|  | 210 |  |  |  |  | 215 |  |  |  |  | 220 |  |  |  |
| Ser | Val | Met | Gln | Val | Thr | Ala | Thr | Asp | Glu | Asp | Asp | Ala | Val | Asn | Thr |
| 225 |  |  |  |  | 230 |  |  |  |  | 235 |  |  |  |  | 240 |

```
Tyr  Asn  Gly  Val  Val  Ala  Tyr  Ser  Ile  His  Ser  Gln  Glu  Pro  Lys  Glu
               245                      250                      255

Pro  His  Asp  Leu  Met  Phe  Thr  Ile  His  Lys  Ser  Thr  Gly  Thr  Ile  Ser
               260                      265                      270

Val  Ile  Ser  Ser  Gly  Leu  Asp  Arg  Glu  Lys  Val  Pro  Glu  Tyr  Arg  Leu
          275                 280                      285

Thr  Val  Gln  Ala  Thr  Asp  Met  Asp  Gly  Glu  Gly  Ser  Thr  Thr  Thr  Ala
     290                      295                 300

Glu  Ala  Val  Val  Gln  Ile  Leu  Asp  Ala  Asn  Asp  Asn  Ala  Pro  Glu  Phe
305                      310                 315                      320

Glu  Pro  Gln  Lys  Tyr  Glu  Ala  Trp  Val  Pro  Glu  Asn  Glu  Val  Gly  His
               325                 330                      335

Glu  Val  Gln  Arg  Leu  Thr  Val  Thr  Asp  Leu  Asp  Val  Pro  Asn  Trp  Pro
               340                 345                      350

Ala  Trp  Arg  Ala  Thr  Tyr  His  Ile  Val  Gly  Gly  Asp  Asp  Gly  Asp  His
               355                 360                      365

Phe  Thr  Ile  Thr  Thr  His  Pro  Glu  Thr  Asn  Gln  Gly  Val  Leu  Thr  Thr
          370                 375                 380

Lys  Lys  Gly  Leu  Asp  Phe  Glu  Ala  Gln  Asp  Gln  His  Thr  Leu  Tyr  Val
385                      390                 395                      400

Glu  Val  Thr  Asn  Glu  Ala  Pro  Phe  Ala  Val  Lys  Leu  Pro  Thr  Ala  Thr
               405                 410                      415

Ala  Thr  Val  Val  Val  His  Val  Lys  Asp  Val  Asn  Glu  Ala  Pro  Val  Phe
               420                 425                      430

Val  Pro  Pro  Ser  Lys  Val  Ile  Glu  Ala  Gln  Glu  Gly  Ile  Ser  Ile  Gly
               435                 440                      445

Glu  Leu  Val  Cys  Ile  Tyr  Thr  Ala  Gln  Asp  Pro  Asp  Lys  Glu  Asp  Gln
     450                      455                 460

Lys  Ile  Ser  Tyr  Thr  Ile  Ser  Arg  Asp  Pro  Ala  Asn  Trp  Leu  Ala  Val
465                      470                 475                      480

Asp  Pro  Asp  Ser  Gly  Gln  Ile  Thr  Ala  Ala  Gly  Ile  Leu  Asp  Arg  Glu
               485                 490                      495

Asp  Glu  Gln  Phe  Val  Lys  Asn  Asn  Val  Tyr  Glu  Val  Met  Val  Leu  Ala
               500                 505                      510

Thr  Asp  Ser  Gly  Asn  Pro  Pro  Thr  Gly  Thr  Gly  Thr  Leu  Leu  Leu
               515                 520                      525

Thr  Leu  Thr  Asp  Ile  Asn  Asp  His  Gly  Pro  Ile  Pro  Glu  Pro  Arg  Gln
     530                      535                 540

Ile  Ile  Ile  Cys  Asn  Gln  Ser  Pro  Val  Pro  Gln  Val  Leu  Asn  Ile  Thr
545                      550                 555                      560

Asp  Lys  Asp  Leu  Ser  Pro  Asn  Ser  Ser  Pro  Phe  Gln  Ala  Gln  Leu  Thr
               565                 570                      575

His  Asp  Ser  Asp  Ile  Tyr  Trp  Met  Ala  Glu  Val  Ser  Glu  Lys  Gly  Asp
               580                 585                      590

Thr  Val  Ala  Leu  Ser  Leu  Lys  Lys  Phe  Leu  Lys  Gln  Asp  Thr  Tyr  Asp
               595                 600                      605

Leu  His  Leu  Ser  Leu  Ser  Asp  His  Gly  Asn  Arg  Glu  Gln  Leu  Thr  Met
     610                      615                 620

Ile  Arg  Ala  Thr  Val  Cys  Asp  Cys  His  Gly  Gln  Val  Phe  Asn  Asp  Cys
625                      630                 635                      640

Pro  Arg  Pro  Trp  Lys  Gly  Gly  Phe  Ile  Leu  Pro  Ile  Leu  Gly  Ala  Val
               645                 650                      655

Leu  Ala  Leu  Leu  Thr  Leu  Leu  Leu  Ala  Leu  Leu  Leu  Leu  Val  Arg  Lys
```

-continued

|  |  |  | | | 660 | | | | | 665 | | | | 670 |
|---|---|---|---|---|---|---|---|---|---|---|---|---|---|---|
| Lys | Arg | Lys 675 | Val | Lys | Glu | Pro | Leu 680 | Leu | Leu | Pro | Glu | Asp 685 | Asp | Thr | Arg |
| Asp | Asn 690 | Val | Phe | Tyr | Tyr | Gly 695 | Glu | Glu | Gly | Gly | Gly 700 | Glu | Glu | Asp | Gln |
| Asp 705 | Tyr | Asp | Ile | Thr | Gln 710 | Leu | His | Arg | Gly | Leu 715 | Glu | Ala | Arg | Pro | Glu 720 |
| Val | Val | Leu | Arg | Asn 725 | Asp | Val | Val | Pro | Thr 730 | Phe | Ile | Pro | Thr | Pro 735 | Met |
| Tyr | Arg | Pro | Arg 740 | Pro | Ala | Asn | Pro | Asp 745 | Glu | Ile | Gly | Asn | Phe 750 | Ile | Ile |
| Glu | Asn | Leu 755 | Lys | Ala | Ala | Asn | Thr 760 | Asp | Pro | Thr | Ala | Pro 765 | Pro | Tyr | Asp |
| Ser | Leu 770 | Met | Val | Phe | Asp | Tyr 775 | Glu | Gly | Ser | Gly | Ser 780 | Asp | Ala | Ala | Ser |
| Leu 785 | Ser | Ser | Leu | Thr | Thr 790 | Ser | Ala | Ser | Asp | Gln 795 | Asp | Gln | Asp | Tyr | Asn 800 |
| Tyr | Leu | Asn | Glu | Trp 805 | Gly | Ser | Arg | Phe | Lys 810 | Lys | Leu | Ala | Asp | Met 815 | Tyr |
| Gly | Gly | Gly | Glu 820 | Asp | Asp | | | | | | | | | | |